(12) United States Patent
Nozaki et al.

(10) Patent No.: US 7,745,182 B2
(45) Date of Patent: Jun. 29, 2010

(54) METHOD FOR PRODUCING β-HYDROXY AMINO ACID AND ENZYME USED THEREFOR

(75) Inventors: Hiroyuki Nozaki, Kawasaki (JP); Shinji Kuroda, Kawasaki (JP); Kunihiko Watanabe, Kawasaki (JP); Kenzo Yokozeki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/345,922

(22) Filed: Dec. 30, 2008

(65) Prior Publication Data

US 2009/0112019 A1    Apr. 30, 2009

Related U.S. Application Data

(62) Division of application No. 11/419,522, filed on May 22, 2006, now Pat. No. 7,507,559.

(30) Foreign Application Priority Data

May 20, 2005    (JP) .............................. 2005-148659

(51) Int. Cl.
  C12P 13/04    (2006.01)
  C12N 9/00    (2006.01)
  C12N 9/10    (2006.01)
(52) U.S. Cl. ....................... 435/106; 435/183; 435/193
(58) Field of Classification Search ....................... None
  See application file for complete search history.

(56) References Cited

U.S. PATENT DOCUMENTS

| 7,320,794 | B2 | 1/2008 | Suzuki et al. |
| 7,351,571 | B2 | 4/2008 | Nakamatsu et al. |
| 2005/0214912 | A1 | 9/2005 | Nozaki et al. |
| 2007/0026504 | A1 | 2/2007 | Suzuki et al. |
| 2008/0241895 | A1 | 10/2008 | Suzuki et al. |

OTHER PUBLICATIONS

Guo et al., (PNAS, 2004, vol. 101 (25): 9205-9210.*
Meinkoth and Wahl (Current Protocols in Molecular Biology, Hybridization Analysis of DNA Blots, pp. 2.10.8-2.10.11, 1993.*
Avenoza, A., et al., "Enantioselective synthesis of (S)- and (R)-α-methylserines: application to the synthesis of (S)- and (R)-N-Boc-N,O-isopropylidene-α-methylserinals," Tetrahedron:Asymmetry 2001;12:949-957, Elsevier Science Ltd., Great Britain.
Colson, P-J, et al., "Asymmetric Synthesis of α-Alkyl-α-amino Acids from Chromium-Carbene-Complex-Derived β-Lactams," J. Org. Chem. 1993;58:5918-5924, American Chemical Society, Washington, DC, US.
Database GENEMBL [Online], Jan. 21, 1986, "Serine hydroxymethyltransferase (EC 2.1.2.1) (Serine Methylase) (SHMT). REF—[ ] NCBI_TaxID=562; [1] Nucleotide Sequence [Genomic DNA]. Strain=K12; Medline=83168944; PubMed=6300791; Plamann M.D., et al.; "Complete nucleotide sequence of the E. coli glyA gene."" XP002396956, Database accession No. POA825; P00477, 2 pp.
Database GENEMBL [Online], Jan. 1, 1996, "Serine hydroxymethyltransferase (EC 2.1.2.1) (Serine methylase) (SHMT). REF—[ ]NCBI_TaxID=408; [1] Nucleotide Sequence [Genomic DNA]. Strain=AM1/NCIMB 9133; Medline=95050239; PubMed=7961431; Chistoserdova, L.V., et al., Genetics of the serine cycle in Methylobacterium extorquens AM1: clo" XP002396957, Database accession No. P50435.
Database EMBL [Online], Database accession No. BX572601, XP-001167168, pp. 1-2.
Database EMBL [Online], Database accession No. L33463, XP-001167167, pp. 1-2.
Ito, Y., et al., "Asymmetric Aldol Reaction of α-Isocyanocarboxylates With Paraformaldehyde Catalyzed by Chiral Ferrocenylphosphine-Gold(I) Complexes: Catalytic Asymmetric Synthesis of α-Alkylserines," Tetrahedron Lett. 1988;29(2):235-238, Pergamon Journals, Ltd., Great Britain.
Najera, C., et al., "Asymmetric Synthesis of α-Methyl α-Amino Acids through Diastereoselective Alkylation under Mild Reaction Conditions of an Iminic Alanine Template with a 1,2,3,6-Tetrahydro-2-pyrazinone Structure," Eur. J. Org. Chem. 2000:2809-2820, Wiley-VCH, Weinheim, Germany.
Ogawa, H., et al., "Serine hydroxymethultransferase and threonine aldolase: are they identical?" Intl. J. Biochem. Cell Biol. 2000;32:289-301.
Seebach, D., et al, "Stereoselektive Alkylierung an C(α) von Serin, Glycerinsäure, Threonin und Weinsäure über heterocyclische Enolate mit exocyclischer Doppelbindung," Helvetica Chimica Acta 1987;70:1194-1216, Wiley-VCH, Weinheim, Germany.
Wilson, E. M., et al., "Metabolism of α-Methylserine," J. Biol. Chem. 1962;237(10):3171-3179, American Society for Biochemistry and Molecular Biology, Bethesda, MD, US.
Wipf, P., et al., "A New Synthesis of α-Methylserine by Nucleophilic Ring-Opening of N-Sulfonyl Aziridines," Tetrahedron Lett. 1995;36(21):3639-3642, Elsevier Science Ltd., Great Britain.
Search Report for EP Patent App. No. 06010436.1 (Sep. 19, 2006).
Office Communication from European Patent App. No. 06010436.1 (Mar. 20, 2008).

* cited by examiner

*Primary Examiner*—Andrew Wang
*Assistant Examiner*—M. D. Younus Meah
(74) *Attorney, Agent, or Firm*—Shelly Guest Cermak; Cermak Nakajima LLP

(57) ABSTRACT

A method for producing β-hydroxy amino acid and its optically-active isomer is provided. The β-hydroxy amino acid is produced by reacting a predetermined D-α-amino acid and 5,10-methylene tetrahydrofolic acid in the presence of an enzyme derived from a microorganism belonging to the genera *Paracoccus*, *Aminobacter*, or *Ensifer*.

14 Claims, 1 Drawing Sheet

SEQUENCE LISTING

```
<160> NUMBER OF SEQ ID NOS: 18

<210> SEQ ID NO 1
<211> LENGTH: 30
<212> TYPE: PRT
<213> ORGANISM: Paracoccus sp.

<400> SEQUENCE: 1

Asn Glu Leu Thr Arg Thr Phe Phe Asn Ser Ser Val His Asp Thr Asp
1               5                   10                  15

Pro Leu Ile Ala Gln Ala Leu Asp Asp Glu Arg Ala Arg Gln
            20                  25                  30

<210> SEQ ID NO 2
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9)..(9)
<223> OTHER INFORMATION: a, c, g or t
<220> FEATURE:
<221> NAME/KEY: misc_feature
<222> LOCATION: (18)..(18)
<223> OTHER INFORMATION: a, c, g or t
<220> FEATURE:
<221> NAME/KEY: misc_feature
```

```
<222> LOCATION: (12)..(12)
<223> OTHER INFORMATION: a, c, g or t
<220> FEATURE:
<221> NAME/KEY: misc_feature
<222> LOCATION: (15)..(15)
<223> OTHER INFORMATION: a, c, g or t

<400> SEQUENCE: 2
aaygarytna cnmgnacntt yttyaa                                        26

<210> SEQ ID NO 3
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: a, c, g or t
<220> FEATURE:
<221> NAME/KEY: misc_feature
<222> LOCATION: (12)..(12)
<223> OTHER INFORMATION: a, c, g or t
<220> FEATURE:
<221> NAME/KEY: misc_feature
<222> LOCATION: (18)..(18)
<223> OTHER INFORMATION: a, c, g or t
<220> FEATURE:
<221> NAME/KEY: misc_feature
<222> LOCATION: (21)..(21)
<223> OTHER INFORMATION: a, c, g or t

<400> SEQUENCE: 3
gtncaygaya cngayccnyt nathgc                                        26

<210> SEQ ID NO 4
<211> LENGTH: 1278
<212> TYPE: DNA
<213> ORGANISM: Paracoccus sp.
<220> FEATURE:
<221> NAME/KEY: CDS
<222> LOCATION: (1)..(1278)

<400> SEQUENCE: 4 atg aac gaa ttg acc agg acc ttc ttc aat tcc tcg gtg cat gac acc    48
Met Asn Glu Leu Thr Arg Thr Phe Phe Asn Ser Ser Val His Asp Thr
1               5                   10                  15 gat ccc ctg atc gcc cag gcg ctg gac gat gaa cgc gcc cgc cag aaa    96
Asp Pro Leu Ile Ala Gln Ala Leu Asp Asp Glu Arg Ala Arg Gln Lys
            20                  25                  30 aac cag atc gag ctg atc gcc tcg gaa aac atc gtg agc cag gcc gtg   144
Asn Gln Ile Glu Leu Ile Ala Ser Glu Asn Ile Val Ser Gln Ala Val
        35                  40                  45 ctg gac gcg ctt ggc cat gag atg acc aac aag acg ctg gaa ggc tat   192
Leu Asp Ala Leu Gly His Glu Met Thr Asn Lys Thr Leu Glu Gly Tyr
    50                  55                  60 ccg ggc aac cgc ttc cac ggt ggc ggg caa ttc gtc gat gtg gtc gaa   240
Pro Gly Asn Arg Phe His Gly Gly Gly Gln Phe Val Asp Val Val Glu
65                  70                  75                  80 cag gcc gcc atc gac cgc gcg aaa cag ctg ttc aac tgc ggc tat gcc   288
Gln Ala Ala Ile Asp Arg Ala Lys Gln Leu Phe Asn Cys Gly Tyr Ala
                85                  90                  95 aac gtc cag ccg cat tcg ggc acg cag gcg aac ctt gcc gtc ttc ttc   336
Asn Val Gln Pro His Ser Gly Thr Gln Ala Asn Leu Ala Val Phe Phe
            100                 105                 110 ctg ctg gtg aag ccg ggc gac cgc atc ctg tcg ctg gat ctg gcc gcc   384
```

```
Leu Leu Val Lys Pro Gly Asp Arg Ile Leu Ser Leu Asp Leu Ala Ala
        115                 120                 125 ggt ggc cac ctg tcg cac ggg atg aag ggc aac ctc tcg ggc cgc tgg        432
Gly Gly His Leu Ser His Gly Met Lys Gly Asn Leu Ser Gly Arg Trp
130                 135                 140 ttc gag gcg cat aac tac aac gtc gat ccg cag aac gaa gtc atc aac        480
Phe Glu Ala His Asn Tyr Asn Val Asp Pro Gln Asn Glu Val Ile Asn
145                 150                 155                 160 tat gac gaa atg gag cgc atc gcc gaa gag gtg aag ccg aaa ctg ctg        528
Tyr Asp Glu Met Glu Arg Ile Ala Glu Glu Val Lys Pro Lys Leu Leu
                165                 170                 175 atc acc ggc ggc tcg gcc tac ccg cgc gaa ctg gat ttc gcc cgc atg        576
Ile Thr Gly Gly Ser Ala Tyr Pro Arg Glu Leu Asp Phe Ala Arg Met
            180                 185                 190 gcg cag atc gcc aag aag gtc ggc gcg ttc ttc atg gtc gac atg gcc        624
Ala Gln Ile Ala Lys Lys Val Gly Ala Phe Phe Met Val Asp Met Ala
        195                 200                 205 cat atc gcc ggt ctg gtc gca ggt ggc gcg cat ccc tcg ccc ttc ccg        672
His Ile Ala Gly Leu Val Ala Gly Gly Ala His Pro Ser Pro Phe Pro
210                 215                 220 cat gcc gat atc gtc acc tgc acc acg acg aaa acc ctg cgc ggc ccg        720
His Ala Asp Ile Val Thr Cys Thr Thr Thr Lys Thr Leu Arg Gly Pro
225                 230                 235                 240 cgc ggc ggc ctg atc ctg acc aac aat gaa gag tgg tac aag aag ctg        768
Arg Gly Gly Leu Ile Leu Thr Asn Asn Glu Glu Trp Tyr Lys Lys Leu
                245                 250                 255 cag acc gcc gtg ttc ccg ggc gtt cag ggg tcg ctg cac tcg aac gtg        816
Gln Thr Ala Val Phe Pro Gly Val Gln Gly Ser Leu His Ser Asn Val
            260                 265                 270 ctg gcg gcc aag gcg atc tgt ctg ggt gag gcg ctg cgc ccc gag ttc        864
Leu Ala Ala Lys Ala Ile Cys Leu Gly Glu Ala Leu Arg Pro Glu Phe
        275                 280                 285 cgc gac tat gtg gcg cag gtc gtc aag aat gcg aag gtg ctg gcc gaa        912
Arg Asp Tyr Val Ala Gln Val Val Lys Asn Ala Lys Val Leu Ala Glu
290                 295                 300 acg ctg acc tcg cgc ggc atc cgc atc gtc tcg ggc ggg acg gat acg        960
Thr Leu Thr Ser Arg Gly Ile Arg Ile Val Ser Gly Gly Thr Asp Thr
305                 310                 315                 320 cat atc gtg ctg ctg gat ctg tcc agc aag ggc ttg aac ggc aag cag       1008
His Ile Val Leu Leu Asp Leu Ser Ser Lys Gly Leu Asn Gly Lys Gln
                325                 330                 335 gcc gag gat gcg ctg gcg cgc gcc aac atc acc tcg aac aag aac ccg       1056
Ala Glu Asp Ala Leu Ala Arg Ala Asn Ile Thr Ser Asn Lys Asn Pro
            340                 345                 350 atc ccg aac gac agc ccg cgc ccg gcg gaa tgg gtc ggc atg cgt ctt       1104
Ile Pro Asn Asp Ser Pro Arg Pro Ala Glu Trp Val Gly Met Arg Leu
        355                 360                 365 ggc gtc tcg gct gcg acc acg cgc ggc atg aaa gag gat gag ttc cgc       1152
Gly Val Ser Ala Ala Thr Thr Arg Gly Met Lys Glu Asp Glu Phe Arg
370                 375                 380 aag ctc ggc aat gtc gtg gcc gac ctc ttg gag gcc gaa agc gca ggc       1200
Lys Leu Gly Asn Val Val Ala Asp Leu Leu Glu Ala Glu Ser Ala Gly
385                 390                 395                 400 aat ggc ccc gag gcc gcc gaa aaa gcc aag gtg acc gtg cgc gaa ctg       1248
Asn Gly Pro Glu Ala Ala Glu Lys Ala Lys Val Thr Val Arg Glu Leu
                405                 410                 415 acc gag gcc ttc ccg gtc tac gcc cac tga                               1278
Thr Glu Ala Phe Pro Val Tyr Ala His
                420                 425
```

<210> SEQ ID NO 5
<211> LENGTH: 425
<212> TYPE: PRT
<213> ORGANISM: Paracoccus sp.

<400> SEQUENCE: 5

Met Asn Glu Leu Thr Arg Thr Phe Phe Asn Ser Ser Val His Asp Thr
1               5                   10                  15

Asp Pro Leu Ile Ala Gln Ala Leu Asp Asp Glu Arg Ala Arg Gln Lys
            20                  25                  30

Asn Gln Ile Glu Leu Ile Ala Ser Glu Asn Ile Val Ser Gln Ala Val
        35                  40                  45

Leu Asp Ala Leu Gly His Glu Met Thr Asn Lys Thr Leu Glu Gly Tyr
    50                  55                  60

Pro Gly Asn Arg Phe His Gly Gly Gln Phe Val Asp Val Val Glu
65                  70                  75                  80

Gln Ala Ala Ile Asp Arg Ala Lys Gln Leu Phe Asn Cys Gly Tyr Ala
                85                  90                  95

Asn Val Gln Pro His Ser Gly Thr Gln Ala Asn Leu Ala Val Phe Phe
            100                 105                 110

Leu Leu Val Lys Pro Gly Asp Arg Ile Leu Ser Leu Asp Leu Ala Ala
        115                 120                 125

Gly Gly His Leu Ser His Gly Met Lys Gly Asn Leu Ser Gly Arg Trp
    130                 135                 140

Phe Glu Ala His Asn Tyr Asn Val Asp Pro Gln Asn Glu Val Ile Asn
145                 150                 155                 160

Tyr Asp Glu Met Glu Arg Ile Ala Glu Val Lys Pro Lys Leu Leu
                165                 170                 175

Ile Thr Gly Gly Ser Ala Tyr Pro Arg Glu Leu Asp Phe Ala Arg Met
            180                 185                 190

Ala Gln Ile Ala Lys Lys Val Gly Ala Phe Phe Met Val Asp Met Ala
        195                 200                 205

His Ile Ala Gly Leu Val Ala Gly Gly Ala His Pro Ser Pro Phe Pro
    210                 215                 220

His Ala Asp Ile Val Thr Cys Thr Thr Thr Lys Thr Leu Arg Gly Pro
225                 230                 235                 240

Arg Gly Gly Leu Ile Leu Thr Asn Asn Glu Glu Trp Tyr Lys Lys Leu
                245                 250                 255

Gln Thr Ala Val Phe Pro Gly Val Gln Gly Ser Leu His Ser Asn Val
            260                 265                 270

Leu Ala Ala Lys Ala Ile Cys Leu Gly Glu Ala Leu Arg Pro Glu Phe
        275                 280                 285

Arg Asp Tyr Val Ala Gln Val Val Lys Asn Ala Lys Val Leu Ala Glu
    290                 295                 300

Thr Leu Thr Ser Arg Gly Ile Arg Ile Val Ser Gly Gly Thr Asp Thr
305                 310                 315                 320

His Ile Val Leu Asp Leu Ser Ser Lys Gly Leu Asn Gly Lys Gln
                325                 330                 335

Ala Glu Asp Ala Leu Ala Arg Ala Asn Ile Thr Ser Asn Lys Asn Pro
            340                 345                 350

Ile Pro Asn Asp Ser Pro Arg Pro Ala Glu Trp Val Gly Met Arg Leu
        355                 360                 365

Gly Val Ser Ala Ala Thr Thr Arg Gly Met Lys Glu Asp Glu Phe Arg
    370                 375                 380

```
Lys Leu Gly Asn Val Val Ala Asp Leu Leu Glu Ala Glu Ser Ala Gly
385                 390                 395                 400

Asn Gly Pro Glu Ala Ala Glu Lys Ala Lys Val Thr Val Arg Glu Leu
                405                 410                 415

Thr Glu Ala Phe Pro Val Tyr Ala His
            420                 425

<210> SEQ ID NO 6
<211> LENGTH: 32
<212> TYPE: DNA
<213> ORGANISM: Artificial
<220> FEATURE:
<223> OTHER INFORMATION: primer

<400> SEQUENCE: 6
cggaattccg gagagaccgc catgaacgaa tt                              32

<210> SEQ ID NO 7
<211> LENGTH: 34
<212> TYPE: DNA
<213> ORGANISM: Artificial
<220> FEATURE:
<223> OTHER INFORMATION: primer

<400> SEQUENCE: 7
ccccaagctt cggaattgaa aaggccgcac aggg                            34

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
atcgarctsa thgcswssga raa                                        23

<210> SEQ ID NO 9
<211> LENGTH: 33
<212> TYPE: DNA
<213> ORGANISM: Artificial
<220> FEATURE:
<223> OTHER INFORMATION: primer

<400> SEQUENCE: 9
gatsagsccs ccscgsggsc cscgsagsgt ytt                             33

<210> SEQ ID NO 10
<211> LENGTH: 1278
<212> TYPE: DNA
<213> ORGANISM: Aminobacter sp.
<220> FEATURE:
<221> NAME/KEY: CDS
<222> LOCATION: (1)..(1278)

<400> SEQUENCE: 10 atg acc gaa cag aca aaa gcc tac ttc aat acc ccg gtg cac gaa cgc    48
Met Thr Glu Gln Thr Lys Ala Tyr Phe Asn Thr Pro Val His Glu Arg
1               5                   10                  15 gac ccg ctg gtg gca cag gcc ctc gac aac gag cgc aag cgc cag cag    96
Asp Pro Leu Val Ala Gln Ala Leu Asp Asn Glu Arg Lys Arg Gln Gln
            20                  25                  30 gac cag atc gaa ctc atc gcg tcc gaa aac atc gtc agc cgc gcc gtg   144
Asp Gln Ile Glu Leu Ile Ala Ser Glu Asn Ile Val Ser Arg Ala Val
```

-continued

|  | 35 | | | | 40 | | | | 45 | | | | | |
|---|---|---|---|---|---|---|---|---|---|---|---|---|---|---|
| ctc | gat | gcc | ctc | ggc | cat | gaa | atg | acg | aac | aag | acg | ctg | gaa | ggc | tac | 192 |
| Leu | Asp | Ala | Leu | Gly | His | Glu | Met | Thr | Asn | Lys | Thr | Leu | Glu | Gly | Tyr |
|  | 50 | | | | 55 | | | | 60 | | | | | |

```
ctc gat gcc ctc ggc cat gaa atg acg aac aag acg ctg gaa ggc tac    192
Leu Asp Ala Leu Gly His Glu Met Thr Asn Lys Thr Leu Glu Gly Tyr
     50              55                  60 cct ggc aac cgc ttc cat ggc ggc ggc cag ttc gtc gac gtc gtc gaa    240
Pro Gly Asn Arg Phe His Gly Gly Gly Gln Phe Val Asp Val Val Glu
65              70                  75                  80 cag gcg gcc atc gac cgg gca aag gaa ctc ttc ggc tgc gcc tac gcc    288
Gln Ala Ala Ile Asp Arg Ala Lys Glu Leu Phe Gly Cys Ala Tyr Ala
                 85                  90                  95 aac gtc cag ccg cat tcg ggc acc cag gcg aat ctc gcc gtg ttc ttc    336
Asn Val Gln Pro His Ser Gly Thr Gln Ala Asn Leu Ala Val Phe Phe
                100                 105                 110 ctg ctg ctg aag ccg ggg gac aag gtt ctc tcg ctc gac ctc gcc gca    384
Leu Leu Leu Lys Pro Gly Asp Lys Val Leu Ser Leu Asp Leu Ala Ala
            115                 120                 125 ggc ggc cac ctg tcg cat ggc atg aag ggc aac ctt tcg ggc cgc tgg    432
Gly Gly His Leu Ser His Gly Met Lys Gly Asn Leu Ser Gly Arg Trp
        130                 135                 140 ttc gaa tcg cac aac tac aat gtc gac ccg gaa acg gaa gtc atc gac    480
Phe Glu Ser His Asn Tyr Asn Val Asp Pro Glu Thr Glu Val Ile Asp
145                 150                 155                 160 tat gac gag atg gag cgc att gcc gaa gag gtg cgc ccg acc ctg ctg    528
Tyr Asp Glu Met Glu Arg Ile Ala Glu Glu Val Arg Pro Thr Leu Leu
                165                 170                 175 atc acc ggc ggc tcc gcc tat ccg cgt gaa ctc gac ttc gaa cgc atg    576
Ile Thr Gly Gly Ser Ala Tyr Pro Arg Glu Leu Asp Phe Glu Arg Met
            180                 185                 190 ggc aag atc gcc aag aag gtt ggc gcc tgg ttc ctc gtc gat atg gcc    624
Gly Lys Ile Ala Lys Lys Val Gly Ala Trp Phe Leu Val Asp Met Ala
        195                 200                 205 cat atc gcc ggc ctc gtc gca ggc ggc gcc cac ccc tcg ccg ttc ccg    672
His Ile Ala Gly Leu Val Ala Gly Gly Ala His Pro Ser Pro Phe Pro
210                 215                 220 cat gcc gat atc gtc acc tgc acc acg acc aag acc ctg cgc ggc ccg    720
His Ala Asp Ile Val Thr Cys Thr Thr Thr Lys Thr Leu Arg Gly Pro
225                 230                 235                 240 cgc ggc ggc ctg atc ctc acg aac aac gaa gcc tgg ttc aag aag ctt    768
Arg Gly Gly Leu Ile Leu Thr Asn Asn Glu Ala Trp Phe Lys Lys Leu
                245                 250                 255 cag tcg gcc gtg ttc ccc ggc gtc cag ggc tcg ctg cac agc aac gtg    816
Gln Ser Ala Val Phe Pro Gly Val Gln Gly Ser Leu His Ser Asn Val
            260                 265                 270 ctt gcc gcg aag gcc gtc tgc ctc ggc gaa gcg ctc cgc ccc gac ttc    864
Leu Ala Ala Lys Ala Val Cys Leu Gly Glu Ala Leu Arg Pro Asp Phe
        275                 280                 285 aag gtc tac gcc gca cag gtc aag gcc aat gcc cgc gtc ctc gcc gag    912
Lys Val Tyr Ala Ala Gln Val Lys Ala Asn Ala Arg Val Leu Ala Glu
    290                 295                 300 acc ctg atc gcc cgc ggc gtg cgg atc gtc tcg ggc ggc acg gat acc    960
Thr Leu Ile Ala Arg Gly Val Arg Ile Val Ser Gly Gly Thr Asp Thr
305                 310                 315                 320 cac atc gtg ctg gtc gac ctg tcg agc aag ggc ctg aac ggc aag cag   1008
His Ile Val Leu Val Asp Leu Ser Ser Lys Gly Leu Asn Gly Lys Gln
                325                 330                 335 gcc gaa gac ctg ctg gcg cgc gcc aac atc acg gcc aac aag aac ccg   1056
Ala Glu Asp Leu Leu Ala Arg Ala Asn Ile Thr Ala Asn Lys Asn Pro
            340                 345                 350 atc ccg aac gat agc ccg cgc ccg gcg gaa tgg gtc ggc atg cgt ctc   1104
```

```
Ile Pro Asn Asp Ser Pro Arg Pro Ala Glu Trp Val Gly Met Arg Leu
            355                 360                 365 ggc gtc tcc gct gcc acc acg cgc ggc atg aag gaa gac gaa ttc cgc    1152
Gly Val Ser Ala Ala Thr Thr Arg Gly Met Lys Glu Asp Glu Phe Arg
    370                 375                 380 acg ctc ggc acc gtc atc gca gac ctg atc gag gcg gaa gcc gcc ggc    1200
Thr Leu Gly Thr Val Ile Ala Asp Leu Ile Glu Ala Glu Ala Ala Gly
385                 390                 395                 400 aat gca gac ggc gtc gtg gaa ggc gcg aag gcg aag gtg gca acg ctg    1248
Asn Ala Asp Gly Val Val Glu Gly Ala Lys Ala Lys Val Ala Thr Leu
                405                 410                 415 acg gcc gct ttc ccg gtc tac gct cac tga                            1278
Thr Ala Ala Phe Pro Val Tyr Ala His
                420                 425

<210> SEQ ID NO 11
<211> LENGTH: 425
<212> TYPE: PRT
<213> ORGANISM: Aminobactor sp.

<400> SEQUENCE: 11

Met Thr Glu Gln Thr Lys Ala Tyr Phe Asn Thr Pro Val His Glu Arg
1               5                   10                  15

Asp Pro Leu Val Ala Gln Ala Leu Asp Asn Glu Arg Lys Arg Gln Gln
            20                  25                  30

Asp Gln Ile Glu Leu Ile Ala Ser Glu Asn Ile Val Ser Arg Ala Val
        35                  40                  45

Leu Asp Ala Leu Gly His Glu Met Thr Asn Lys Thr Leu Glu Gly Tyr
    50                  55                  60

Pro Gly Asn Arg Phe His Gly Gly Gln Phe Val Asp Val Val Glu
65                  70                  75                  80

Gln Ala Ala Ile Asp Arg Ala Lys Glu Leu Phe Gly Cys Ala Tyr Ala
                85                  90                  95

Asn Val Gln Pro His Ser Gly Thr Gln Ala Asn Leu Ala Val Phe Phe
            100                 105                 110

Leu Leu Leu Lys Pro Gly Asp Lys Val Leu Ser Leu Asp Leu Ala Ala
        115                 120                 125

Gly Gly His Leu Ser His Gly Met Lys Gly Asn Leu Ser Gly Arg Trp
    130                 135                 140

Phe Glu Ser His Asn Tyr Asn Val Asp Pro Glu Thr Glu Val Ile Asp
145                 150                 155                 160

Tyr Asp Glu Met Glu Arg Ile Ala Glu Glu Val Arg Pro Thr Leu Leu
                165                 170                 175

Ile Thr Gly Gly Ser Ala Tyr Pro Arg Glu Leu Asp Phe Glu Arg Met
            180                 185                 190

Gly Lys Ile Ala Lys Lys Val Gly Ala Trp Phe Leu Val Asp Met Ala
        195                 200                 205

His Ile Ala Gly Leu Val Ala Gly Gly Ala His Pro Ser Pro Phe Pro
    210                 215                 220

His Ala Asp Ile Val Thr Cys Thr Thr Thr Lys Thr Leu Arg Gly Pro
225                 230                 235                 240

Arg Gly Gly Leu Ile Leu Thr Asn Asn Glu Ala Trp Phe Lys Lys Leu
                245                 250                 255

Gln Ser Ala Val Phe Pro Gly Val Gln Gly Ser Leu His Ser Asn Val
            260                 265                 270

Leu Ala Ala Lys Ala Val Cys Leu Gly Glu Ala Leu Arg Pro Asp Phe
```

-continued

```
                275                 280                 285
Lys Val Tyr Ala Ala Gln Val Lys Ala Asn Ala Arg Val Leu Ala Glu
    290                 295                 300

Thr Leu Ile Ala Arg Gly Val Arg Ile Val Ser Gly Gly Thr Asp Thr
305                 310                 315                 320

His Ile Val Leu Val Asp Leu Ser Ser Lys Gly Leu Asn Gly Lys Gln
                325                 330                 335

Ala Glu Asp Leu Leu Ala Arg Ala Asn Ile Thr Ala Asn Lys Asn Pro
            340                 345                 350

Ile Pro Asn Asp Ser Pro Arg Pro Ala Glu Trp Val Gly Met Arg Leu
        355                 360                 365

Gly Val Ser Ala Ala Thr Thr Arg Gly Met Lys Glu Asp Glu Phe Arg
    370                 375                 380

Thr Leu Gly Thr Val Ile Ala Asp Leu Ile Glu Ala Glu Ala Ala Gly
385                 390                 395                 400

Asn Ala Asp Gly Val Val Glu Gly Ala Lys Ala Lys Val Ala Thr Leu
                405                 410                 415

Thr Ala Ala Phe Pro Val Tyr Ala His
            420                 425

<210> SEQ ID NO 12
<211> LENGTH: 32
<212> TYPE: DNA
<213> ORGANISM: Artificial
<220> FEATURE:
<223> OTHER INFORMATION: primer

<400> SEQUENCE: 12
cgggatccgg agacaggtca tgaccgaaca ga                              32

<210> SEQ ID NO 13
<211> LENGTH: 34
<212> TYPE: DNA
<213> ORGANISM: Artificial
<220> FEATURE:
<223> OTHER INFORMATION: primer

<400> SEQUENCE: 13
aaactgcagt cagtgagcgt agaccgggaa agcg                            34

<210> SEQ ID NO 14
<211> LENGTH: 29
<212> TYPE: DNA
<213> ORGANISM: Artificial
<220> FEATURE:
<223> OTHER INFORMATION: primer

<400> SEQUENCE: 14
acsaayaart aygcsgargg stayccsgg                                  29

<210> SEQ ID NO 15
<211> LENGTH: 1278
<212> TYPE: DNA
<213> ORGANISM: Ensifer sp.
<220> FEATURE:
<221> NAME/KEY: CDS
<222> LOCATION: (1)..(1278)

<400> SEQUENCE: 15 atg gat cac gcc acc aga gcg cat ttt act atg act gtt gga gaa gtt      48
Met Asp His Ala Thr Arg Ala His Phe Thr Met Thr Val Gly Glu Val
1               5                   10                  15
```

```
gac cct ctc ctg gcc gat gcc ctt gca tcg gaa cgg ggc cgt caa caa      96
Asp Pro Leu Leu Ala Asp Ala Leu Ala Ser Glu Arg Gly Arg Gln Gln
         20                  25                  30 aat cag atc gag ttg atc gcc tcg gag aac atc gtc agc cgc gcg gtc     144
Asn Gln Ile Glu Leu Ile Ala Ser Glu Asn Ile Val Ser Arg Ala Val
             35                  40                  45 ctc gac gca ctg ggg cac gag atc acc aac aag acg ctt gaa ggc tat     192
Leu Asp Ala Leu Gly His Glu Ile Thr Asn Lys Thr Leu Glu Gly Tyr
 50                  55                  60 ccc ggc aac cgc ttc cat ggt ggc ggc cag ttc gtc gat atc gcg gag     240
Pro Gly Asn Arg Phe His Gly Gly Gly Gln Phe Val Asp Ile Ala Glu
65                  70                  75                  80 cag gcg gcg atc gac cgc gcc aaa cag ctc ttt aac tgc ggt tac gcc     288
Gln Ala Ala Ile Asp Arg Ala Lys Gln Leu Phe Asn Cys Gly Tyr Ala
                 85                  90                  95 aac gtg cag ccc cat tcg ggc acc cag gcc aac ctc gcc gtt ttc ttc     336
Asn Val Gln Pro His Ser Gly Thr Gln Ala Asn Leu Ala Val Phe Phe
            100                 105                 110 ctg ctc ctg aag cca ggc gag aag gtg ctt tcg ctt gat ctg gca gca     384
Leu Leu Leu Lys Pro Gly Glu Lys Val Leu Ser Leu Asp Leu Ala Ala
        115                 120                 125 ggc ggt cat ctc tcg cac ggc atg aaa gcg aac ctc tcg ggt cgc tgg     432
Gly Gly His Leu Ser His Gly Met Lys Ala Asn Leu Ser Gly Arg Trp
    130                 135                 140 ttc gac gcc act aac tac aac gtc aat ccg cag aac gaa gtc att gat     480
Phe Asp Ala Thr Asn Tyr Asn Val Asn Pro Gln Asn Glu Val Ile Asp
145                 150                 155                 160 ctc gac gag atg gag cgg ctt gcc gag gaa atc cga ccg aaa ctg ctg     528
Leu Asp Glu Met Glu Arg Leu Ala Glu Glu Ile Arg Pro Lys Leu Leu
                165                 170                 175 atc aca ggc ggt tcc gca tac ccg cga gag ttg gac ttc gaa cgc atg     576
Ile Thr Gly Gly Ser Ala Tyr Pro Arg Glu Leu Asp Phe Glu Arg Met
            180                 185                 190 tcg agg atc gcg aag aag gtc ggc gca tac ttc ctg gtc gac atg gcc     624
Ser Arg Ile Ala Lys Lys Val Gly Ala Tyr Phe Leu Val Asp Met Ala
        195                 200                 205 cat atc gca ggt ctc gtt gca ggc ggc gtg cat ccg tcg ccg ttc ccg     672
His Ile Ala Gly Leu Val Ala Gly Gly Val His Pro Ser Pro Phe Pro
    210                 215                 220 cat gcg gat att gtg aca tgc acc acg act aag acg ctt cgc ggt ccc     720
His Ala Asp Ile Val Thr Cys Thr Thr Thr Lys Thr Leu Arg Gly Pro
225                 230                 235                 240 cgc ggg ggc tta atc ctc acc aac aat gag gag tgg tac aag aaa ctg     768
Arg Gly Gly Leu Ile Leu Thr Asn Asn Glu Glu Trp Tyr Lys Lys Leu
                245                 250                 255 cag gcc gcc gtt ttc ccc ggt gtt cag ggg tcg ctg cac agc aac gtt     816
Gln Ala Ala Val Phe Pro Gly Val Gln Gly Ser Leu His Ser Asn Val
            260                 265                 270 ctt gcg gca aag gcg atc tgc ctc ggc gag gcg atg ctc gat gac ttt     864
Leu Ala Ala Lys Ala Ile Cys Leu Gly Glu Ala Met Leu Asp Asp Phe
        275                 280                 285 aag gtc tac gca cgg cag gtg gtc gca aac gcg aag gtt ctc gcg aac     912
Lys Val Tyr Ala Arg Gln Val Val Ala Asn Ala Lys Val Leu Ala Asn
    290                 295                 300 acg ctt gcc gaa cgc ggc gtc cgg atc gtt tcg ggc ggg acc gac acc     960
Thr Leu Ala Glu Arg Gly Val Arg Ile Val Ser Gly Gly Thr Asp Thr
305                 310                 315                 320 cac atc gtc ctc ctc gat ctt gcg agc aag gga ctg ctt gga aaa cag    1008
His Ile Val Leu Leu Asp Leu Ala Ser Lys Gly Leu Leu Gly Lys Gln
```

-continued

```
            325                 330                 335
gct gag acg ttg ctc gcc aag gcg aat atc acc tct aac aag aac ccg    1056
Ala Glu Thr Leu Leu Ala Lys Ala Asn Ile Thr Ser Asn Lys Asn Pro
            340                 345                 350 atc cct ggc gac agc ccg cgt cct ccg gaa tgg gtc ggt atg cgc ctc    1104
Ile Pro Gly Asp Ser Pro Arg Pro Pro Glu Trp Val Gly Met Arg Leu
            355                 360                 365 ggc tca tca gcg gca acg act cgg ggc ttg aag gag gcg gag ttc cga    1152
Gly Ser Ser Ala Ala Thr Thr Arg Gly Leu Lys Glu Ala Glu Phe Arg
            370                 375                 380 gtg ctg ggt acc gtg atc gcg gac ctc att gac gcc gag gtc gcc ggc    1200
Val Leu Gly Thr Val Ile Ala Asp Leu Ile Asp Ala Glu Val Ala Gly
385                 390                 395                 400 aag gcc gac gac gtc gtc gaa ggc gcc aag gcc aaa ata gcc gag ctg    1248
Lys Ala Asp Asp Val Val Glu Gly Ala Lys Ala Lys Ile Ala Glu Leu
                    405                 410                 415 acg aac acg ttc ccg gtc tac ggg cag taa                            1278
Thr Asn Thr Phe Pro Val Tyr Gly Gln
                420                 425

<210> SEQ ID NO 16
<211> LENGTH: 425
<212> TYPE: PRT
<213> ORGANISM: Ensifer sp.

<400> SEQUENCE: 16

Met Asp His Ala Thr Arg Ala His Phe Thr Met Thr Val Gly Glu Val
1               5                   10                  15

Asp Pro Leu Leu Ala Asp Ala Leu Ala Ser Glu Arg Gly Arg Gln Gln
                20                  25                  30

Asn Gln Ile Glu Leu Ile Ala Ser Glu Asn Ile Val Ser Arg Ala Val
            35                  40                  45

Leu Asp Ala Leu Gly His Glu Ile Thr Asn Lys Thr Leu Glu Gly Tyr
        50                  55                  60

Pro Gly Asn Arg Phe His Gly Gly Gln Phe Val Asp Ile Ala Glu
65                  70                  75                  80

Gln Ala Ala Ile Asp Arg Ala Lys Gln Leu Phe Asn Cys Gly Tyr Ala
                85                  90                  95

Asn Val Gln Pro His Ser Gly Thr Gln Ala Asn Leu Ala Val Phe Phe
            100                 105                 110

Leu Leu Leu Lys Pro Gly Glu Lys Val Leu Ser Leu Asp Leu Ala Ala
        115                 120                 125

Gly Gly His Leu Ser His Gly Met Lys Ala Asn Leu Ser Gly Arg Trp
    130                 135                 140

Phe Asp Ala Thr Asn Tyr Asn Val Asn Pro Gln Asn Glu Val Ile Asp
145                 150                 155                 160

Leu Asp Glu Met Glu Arg Leu Ala Glu Glu Ile Arg Pro Lys Leu Leu
                165                 170                 175

Ile Thr Gly Gly Ser Ala Tyr Pro Arg Glu Leu Asp Phe Glu Arg Met
            180                 185                 190

Ser Arg Ile Ala Lys Lys Val Gly Ala Tyr Phe Leu Val Asp Met Ala
        195                 200                 205

His Ile Ala Gly Leu Val Ala Gly Gly Val His Pro Ser Pro Phe Pro
    210                 215                 220

His Ala Asp Ile Val Thr Cys Thr Thr Thr Lys Thr Leu Arg Gly Pro
225                 230                 235                 240
```

```
Arg Gly Gly Leu Ile Leu Thr Asn Asn Glu Glu Trp Tyr Lys Lys Leu
            245                 250                 255

Gln Ala Ala Val Phe Pro Gly Val Gln Gly Ser Leu His Ser Asn Val
            260                 265                 270

Leu Ala Ala Lys Ala Ile Cys Leu Gly Glu Ala Met Leu Asp Asp Phe
            275                 280                 285

Lys Val Tyr Ala Arg Gln Val Val Ala Asn Ala Lys Val Leu Ala Asn
            290                 295                 300

Thr Leu Ala Glu Arg Gly Val Arg Ile Val Ser Gly Gly Thr Asp Thr
305                 310                 315                 320

His Ile Val Leu Leu Asp Leu Ala Ser Lys Gly Leu Leu Gly Lys Gln
                325                 330                 335

Ala Glu Thr Leu Leu Ala Lys Ala Asn Ile Thr Ser Asn Lys Asn Pro
                340                 345                 350

Ile Pro Gly Asp Ser Pro Arg Pro Pro Glu Trp Val Gly Met Arg Leu
                355                 360                 365

Gly Ser Ser Ala Ala Thr Thr Arg Gly Leu Lys Glu Ala Glu Phe Arg
    370                 375                 380

Val Leu Gly Thr Val Ile Ala Asp Leu Ile Asp Ala Glu Val Ala Gly
385                 390                 395                 400

Lys Ala Asp Asp Val Val Glu Gly Ala Lys Ala Lys Ile Ala Glu Leu
                405                 410                 415

Thr Asn Thr Phe Pro Val Tyr Gly Gln
                420                 425

<210> SEQ ID NO 17
<211> LENGTH: 33
<212> TYPE: DNA
<213> ORGANISM: Artificial
<220> FEATURE:
<223> OTHER INFORMATION: primer

<400> SEQUENCE: 17
cggaattcgg agaacgagat ggatcacgcc acc                              33

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
cgggatcctt actgcccgta gaccgggaac gtg                              33
```

METHOD FOR PRODUCING β-HYDROXY AMINO ACID AND ENZYME USED THEREFOR

This application is a divisional under 35 U.S.C. §120 to U.S. patent application Ser. No. 11/419,522, filed on May 22, 2006, now U.S. Pat. No. 7,507,559, which claims priority under 35 U.S.C. §119(a) to Japanese Patent Application No. 2005-148659, filed on May 20, 2005, the entirety of which is incorporated by reference. The Sequence Listing filed electronically herewith is also hereby incorporated by reference in its entirety (File Name: US-288D2_Seq_List; File Size: 32 KB; Date Created: Dec. 30, 2008).

BACKGROUND OF THE INVENTION

1. Field of the Invention

The present invention relates to a method for producing β-hydroxy amino acid and in particular, to a method for producing the β-hydroxy amino acid using a novel enzyme.

2. Brief Description of the Related Art

Amino acids such as β-hydroxy amino acid and amino acids having optical activity at an α-position are expected to be used as intermediates for pharmaceuticals. Examples of methods for producing optically-active α-alkyl serine derivatives which are optically-active amino acid derivatives having two different substituents at the α-position, and salts thereof, include the following methods:

1) asymmetric alkylation of an optically-active oxazolidine compound obtained from the optically-active serine derivative and pivalaldehyde (Seebach et al., *Helvetica Chimica Acta*, 1987, 70:1194-1216);

2) asymmetric aldol reaction of α-isocyano carboxylic acid ester and paraformaldehyde with an optically-active metal catalyst (Yoshihiko et al., *Tetrahedron Letters*, 1988, 29:235-238);

3) asymmetric alkylation of optically-active β-lactam compounds obtained from an optically active oxazolidine chromium carbene complex and an oxazine compound (Colson et al., *Journal of Organic Chemistry*, 1993, 58:5918-5924);

4) asymmetric ring-opening reaction of an optically-active aziridine compound (Wipf et al., *Tetrahedron Letters*, 1995, 36:3639-3642)

5) asymmetric alkylation of an optically-active pyrazinone compound obtained from an optically-active valine derivative and an optically-active alanine derivative (Najera et al., *European Journal of Organic Chemistry*, 2000, 2809-2820); and 6) Sharpless asymmetric dihydroxylation of a 2-methyl-2-propenoic acid derivative followed by introduction of a resulting optically-active diol compound into an optically-active azido compound for reduction (Avenoza et al., *Tetrahedron Asymmetry*, 2001, 12:949-957).

α-Methyl-L-serine is one of the promising substances which may be used as an intermediate of a medicament. In one of the known methods for producing α-methyl-L-serine by means of an enzymatic reaction, D-alanine and 5,10-methylenetetrahydrofolic acid are used as the materials, and 2-methyl serine hydroxymethyl transferase (EC 2.1.2.7) is used as the enzyme. However, this method utilizes an enzyme derived from a microorganism belonging to genus *Pseudomonas*, and requires the addition of expensive α-methyl-serine in order to produce an enzyme in a cultivation medium (Wilson et al., *J. Biol. Chem.* 237:3171-3179). In addition, utilizing the enzyme derived from the microorganism belonging to genus *Pseudomonas*, α-methyl-L-serine is obtained from 4 mmol of material (D-Ala) with a yield of as low as 11%, which does not satisfy the requirements for practical use.

SUMMARY OF THE INVENTION

As mentioned above, many studies have been conducted on a wide variety of methods for producing optically-active amino acids. Nevertheless, a simpler, more effective, and cost-efficient method for producing a variety of optically-active amino acids and β-hydroxy amino acid is desirable. The object of the present invention is to provide a new simpler method for producing β-hydroxy amino acid and optically-active β-hydroxy amino acid, as well as an enzyme which may be used in the method.

A novel method has been developed for producing a β-hydroxy amino acid, and a new protein has been found which catalyzes the reaction in a reaction system where 5,10-methylenetetrahydrofolic acid and/or a predetermined aldehyde are involved, and using a D-amino acid as a starting material. It has also been determined that this protein can be used to conveniently produce a β-hydroxy amino acid. In addition, it has also been determined that production with this protein results in selective production of an L-amino acid if the product is an amino acid having optical activity. The present invention provides a method for producing a β-hydroxy amino acid and an enzyme used in the method, as mentioned below.

It is an object of the present invention to provide a method for producing a β-hydroxy amino acid of formula (III):

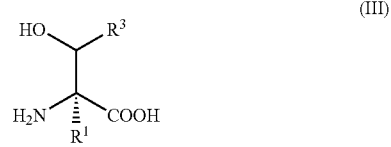

comprising reacting a D-α-amino acid of formula (I):

with 5,10-methylenetetrahydrofolic acid and/or an aldehyde of formula (II):

in the presence of an enzyme isolated from a microorganism belonging to a genus selected from the group consisting of *Paracoccus, Aminobacter*, and *Ensifer*, and wherein $R^1$ and $R^2$ are each selected from the group consisting of an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^3$ is selected from the group consisting of hydrogen, an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^1$, $R^2$, and $R^3$ may be either linear or branched, and may have a substituent.

It is a further object of the present invention to provide the method described above, wherein said D-α-amino acid is D-α-alanine and said β-hydroxy amino acid is α-methyl-L-serine.

It is even a further object of the present invention to provide a method for producing β-hydroxy amino acid of formula (III):

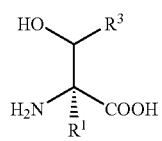

comprising reacting a D-α-amino acid of formula (I):

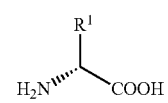

with 5,10-methylenetetrahydrofolic acid and/or an aldehyde of formula (II):

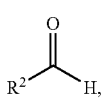

in the presence of a protein selected from the group consisting of:
(A) a protein comprising the amino acid sequence of SEQ ID NO: 5;
(B) a variant protein of the amino acid sequence of SEQ ID NO: 5, which is able to catalyze the reaction to produce the β-hydroxy amino acid of formula (III);
(C) a protein comprising the amino acid sequence of SEQ ID NO: 11;
(D) a variant protein of the amino acid sequence of SEQ ID NO: 11, which is able to catalyze the reaction to produce the β-hydroxy amino acid of formula (III);
(E) a protein comprising the amino acid sequence of SEQ ID NO: 16; and
(F) a variant protein of the amino acid sequence of SEQ ID NO: 16, which is able to catalyze the reaction to produce the β-hydroxy amino acid of formula (III), and wherein, $R^1$ and $R^2$ are each selected from the group consisting of an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^3$ is selected from the group consisting of hydrogen, an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^1$, $R^2$, and $R^3$ may be either linear or branched, and may have a substituent.

It is even a further object of the present invention to provide the method as described above, wherein said D-α-amino acid is D-α-alanine and said β-hydroxy amino acid is α-methyl-L-serine.

It is even a further object of the present invention to provide a protein isolated from a microorganism belonging to a genus selected from the group consisting of *Paracoccus*, *Aminobacter*, and *Ensifer*, and wherein said protein is able to catalyze the reaction of a D-α-amino acid of formula (I):

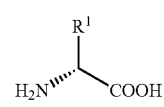

with 5,10-methylenetetrahydrofolic acid and/or an aldehyde of formula (II):

to produce a β-hydroxy amino acid of formula (III):

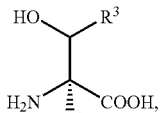

and
wherein $R^1$ and $R^2$ are each selected from the group consisting of an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^3$ is selected from the group consisting of hydrogen, an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^1$, $R^2$, and $R^3$ may be either linear or branched, and may have a substituent.

It is even a further object of the present invention to provide a protein which is able to catalyze the reaction of a D-α-amino acid of formula (I):

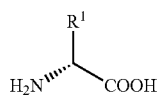

(I)

with 5,10-methylenetetrahydrofolic acid and/or an aldehyde of formula (II):

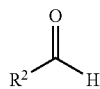

(II)

to produce a β-hydroxy amino acid of formula (III):

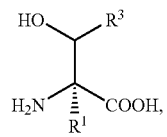

(III)

and wherein $R^1$ and $R^2$ are each selected from the group consisting of an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^3$ is selected from the group consisting of hydrogen, an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^1$, $R^2$, and $R^3$ may be either linear or branched, and may have a substituent, and wherein said protein is selected from the group consisting of:
(A) a protein comprising the amino acid sequence of SEQ ID NO: 5, or a variant protein thereof;
(B) a protein comprising the amino acid sequence of SEQ ID NO: 11, or a variant protein thereof;
(C) a protein comprising the amino acid sequence of SEQ ID NO: 16, or a variant protein thereof.

It is even a further object of the present invention to provide a polynucleotide encoding the protein as described above.

It is even a further object of the present invention to provide a polynucleotide selected from the group consisting of:
(a) a polynucleotide comprising the nucleotide sequence of SEQ ID NO: 4;
(b) a polynucleotide which hybridizes with a nucleotide sequence complementary to that of SEQ ID NO: 4 under stringent conditions, and which encodes a protein which is able to catalyze the reaction of D-α-amino acid of formula (I) with 5,10-methylenetetrahydrofolic acid and/or an aldehyde of formula (II) to produce β-hydroxy amino acid of formula (III);
(c) a polynucleotide comprising the nucleotide sequence of SEQ ID NO: 10;
(d) a polynucleotide which hybridizes with a nucleotide sequence complementary to that of SEQ ID NO: 10 under stringent conditions, and which encodes a protein which is able to catalyze the reaction of D-α-amino acid of formula (I) with 5,10-methylenetetrahydrofolic acid and/or an aldehyde of formula (II) to produce β-hydroxy amino acid of formula (III);
(e) a polynucleotide comprising the nucleotide sequence of SEQ ID NO: 15;
(f) a polynucleotide which hybridizes with a nucleotide sequence complementary to that of SEQ ID NO: 15 under stringent conditions, and which encodes a protein which is able to catalyze the reaction of D-α-amino acid of formula (I) with 5,10-methylenetetrahydrofolic acid and/or an aldehyde of formula (II) to produce β-hydroxy amino acid of formula (III); and wherein formula (I) is:

(I)

wherein formula (II) is:

(II)

wherein formula (III) is:

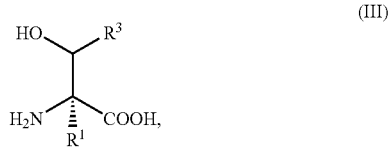

and wherein, $R^1$ and $R^2$ are each selected from the group consisting of an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, and wherein $R^3$ is selected from the group consisting of hydrogen, an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical with any of the aforementioned groups except for containing a hetero atom in the carbon skeleton thereof, and a group identical with any of the aforementioned groups except for containing a carbon-carbon unsaturated bond in the carbon skeleton thereof, and wherein $R^1$, $R^2$, and $R^3$ may be either linear or branched and may have a substituent.

It is even a further object of the present invention to provide a recombinant polynucleotide having the polynucleotide as described above incorporated therein.

It is even a further object of the present invention to provide a transformant having the polynucleotide as described above incorporated therein.

It is even a further object of the present invention to provide a recombinant polynucleotide having the polynucleotide as described above incorporated therein.

It is even a further object of the present invention to provide a transformant having the polynucleotide according to claim 11 incorporated therein.

It is even a further object of the present invention to provide the method as described above, wherein said variant protein of the amino acid sequence of SEQ ID NO. 5 is 90% homologous to SEQ ID NO. 5, said variant protein of the amino acid sequence of SEQ ID NO. 11 is 90% homologous to SEQ ID NO. 11, and said variant protein of the amino acid sequence of SEQ ID NO. 16 is 90% homologous to SEQ ID NO. 16.

It is even a further object of the present invention to provide the protein as described above, wherein said variant protein in (A) is 90% homologous to SEQ ID NO. 5, said variant protein of (B) is 90% homologous to SEQ ID NO. 11, and said variant protein of (C) is 90% homologous to SEQ ID NO. 16.

The present invention allows a β-hydroxy amino acid to be produced by simple procedures.

In the production of an optically active β-hydroxy amino acids, the present invention allows selective production of an L-amino acid. Thus, the present invention provides an efficient method for producing the L-amino acid. Furthermore, the present invention may achieve the production of the recombinant and transformant of the novel enzyme, leading to low-cost, large-scale production of amino acids.

The above and other objects, features, advantages and technical and industrial significance of this invention will be better understood by reading the following detailed description of the presently preferred embodiments of the invention, when considered in connection with the accompanying drawings.

DETAILED DESCRIPTION OF EXEMPLARY EMBODIMENTS

Figure 1:
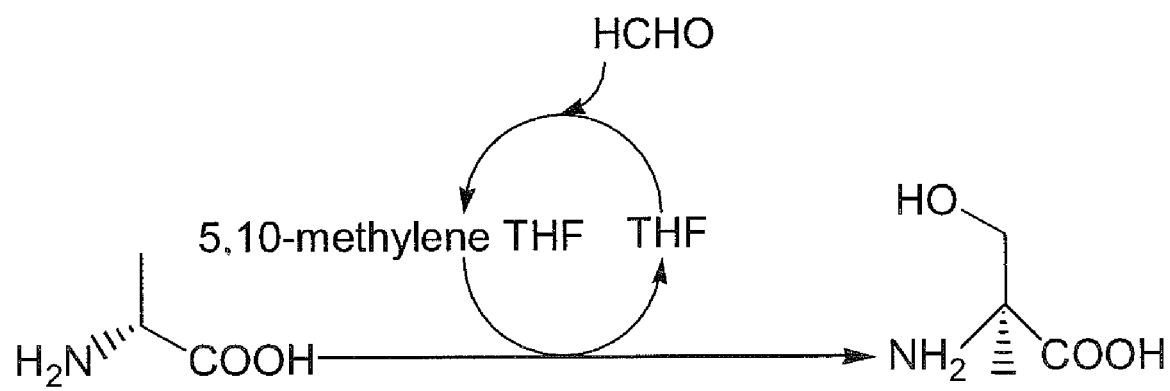
FIG. 1 is a scheme showing the reaction system according to one embodiment of the present invention.

The embodiments according to the present invention will be described hereinbelow with reference to the best mode of carrying out the invention. It should be noted that various types of genetic engineering approaches are described in many standard experimental manuals, such as Molecular Cloning: A Laboratory Manual, $3^{rd}$ edition, Cold Spring Harbor press (Jan. 15, 2001), *Saibo Kogaku Handbook* (Cellular Engineering Handbook), Toshio KUROKI et al., Yodosya (1992), and *Shin Idenshi Kogaku Handbook* (New Gene Engineering Handbook), $3^{rd}$ edition, Matsumura et al., Yodosya (1999), and by reference to these manuals, a person skilled in the art may easily use these approaches.

In the specification, SEQ ID NOs. refers to the sequence numbers in a sequence listing unless otherwise stated. In the specification, an enzyme is a protein which is able to catalyze a chemical reaction.

In the method of the present invention for producing the β-hydroxy amino acid, a D-α-amino acid of formula (I), and 5,10-methylenetetrahydrofolic acid and/or an aldehyde of formula (II) are reacted. In the specification and the accompanying drawing, tetrahydrofolic acid may be simply referred to as THF. Similarly, 5,10-methylenetetrahydrofolic acid may be simply referred to as 5,10-methylene THF. 5,10-methylene THF and/or the aldehyde of formula (II) may be used in combination or alone.

Specific examples of $R^1$ and/or $R^2$ may include the following:

Examples of the alkyl group with 1 to 6 carbon atoms may include a methyl group, an ethyl group, a n-propyl group, an isopropyl group, a n-butyl group, an isobutyl group, a sec-butyl group, a tert-butyl group, a n-pentyl group, an isopentyl group, a neo-pentyl group, a n-hexyl group, and an isohexyl group. Examples of the aryl group with 6 to 14 carbon atoms may include a phenyl group, a tolyl group, a xylyl group, a biphenyl group, a naphthyl group, an anthryl group, and a phenanthryl group.

Examples of the cycloalkyl group with 3 to 10 carbon atoms may include a cyclopropyl group, a cyclobutyl group, a cyclopentyl group, a cyclohexyl group, a cycloheptanyl group, a cyclooctanyl group, a cyclononanyl group, and a cyclodecanyl group.

Examples of the aralkyl group with 7 to 19 carbon atoms may include phenylalkyl groups such as a benzyl group, a benzhydryl group, a phenethyl group and a trityl group, a cinnamyl group, a stylyl group, and a naphthylalkyl group.

Examples of the alkoxyalkyl group with 2 to 11 carbon atoms may include an alkyl group with 1 to 10 carbon atoms which has a substituent selected from the group consisting of a methoxy group, an ethoxy group, a propoxy group, an isopropoxy group, a butoxy group, a pentyloxy group, a phenoxy group, a heptoxy group, an octoxy group, a nonanoxy group, and decanoxy group.

$R^1$ and/or $R^2$ may be a group which is identical with any of the aforementioned hydrocarbon groups except for containing a hetero atom in its carbon skeleton. Examples of the hetero atom may include an oxygen atom, a nitrogen atom, and a sulfur atom.

One embodiment of $R^1$ and/or $R^2$ containing the hetero atom in its carbon skeleton may be a heteroring-containing hydrocarbon group. The heteroring-containing hydrocarbon group is a cyclic hydrocarbon group, wherein a ring of the cyclic moiety contains the hetero atom. Examples of the heteroring-containing hydrocarbon group may include heterocyclic groups such as a heteroaryl group with or without aromaticity and may be either monocyclic or polycyclic group. Specific examples of the heteroring-containing hydrocarbon group may include a furyl group, a thienyl group, a pyridyl group, a piperidyl group, a piperidino group, a morpholino group, an indolyl group, an imidazolyl group, and an alkyl group substituted by any of these heterocyclic groups.

$R^1$ and/or $R^2$ may also be a hydrocarbon group which is identical with any of the aforementioned groups except for containing an unsaturated carbon-carbon bond in its carbon skeleton.

In addition, the aforementioned $R^1$ and/or $R^2$ may be linear or branched. Moreover, $R^1$ and/or $R^2$ may be the aforementioned hydrocarbon group which is substituted by the following group or to which the following group is added: one or more groups which include a halogen atom, an alkyl group with up to 3 carbon atoms, an alkoxyl group with up to 3 carbon atoms, a keto group (=O), a hydroxyl group (—OH), a thiol group (—SH), an amino group (—$NH_2$), an amido group (—$CONH_2$), an imino group (=NH), and a hydrazino group (—$NHNH_2$).

Examples of the D-α-amino acid of formula (I) may include alanine, valine, leucine, isoleucine, serine, threonine, cysteine, methionine, asparagine, glutamine, phenylalanine, tyrosine, tryptophan, aspartic acid, glutamic acid, lysine, arginine, histidine, 2-amino-n-butyric acid, all of which are of D-α-type, preferably, alanine, serine, and 2-amino-n-butyric acid, and more preferably, alanine.

Formula (II) does not include formaldehyde (i.e., wherein $R^2$ is hydrogen). However, formaldehyde may be used to generate 5,10-methylene THF. 5,10-methylene THF may be easily obtained by reacting formaldehyde with THF. 5,10-methylene THF also reacts with a D-amino acid of formula (I) to produce THF. This means that 5,10-THF and THF may form a cyclic reaction system. According to the method of the present invention, the THF cyclic reaction system may be used as a secondary reaction system.

In formula (III), $R^1$ is the same as $R^1$ in formula (I). In formula (III), $R^3$ may be hydrogen, an alkyl group with 1 to 6 carbon atoms, an aryl group with 6 to 14 carbon atoms, a cycloalkyl group with 3 to 10 carbon atoms, an aralkyl group with 7 to 19 carbon atoms, an alkoxyalkyl group with 2 to 11 carbon atoms, a group identical to any of the aforementioned groups except for containing a hetero atom in the carbon skeleton thereof, and a group identical to any of the aforementioned groups except for containing a carbon-carbon unsaturated bond in the carbon skeleton thereof, wherein these groups may be either linear or branched and may have a substituent. Specific examples of the hydrocarbon groups other than hydrogen are the same as those in the aforementioned examples for $R^1$ and $R^2$.

A preferable embodiment of the present invention may be a reaction system in which D-α-alanine reacts with 5,10-methylene THF to produce α-methyl-L-serine. FIG. 1 shows a specific example of the reaction system.

As shown in FIG. 1, THF reacts with formaldehyde to produce 5,10-methylene THF. 5,10-methylene THF is reacted with D-α-alanine in the presence of a predetermined enzyme. Through the reaction, D-α-methyl serine and THF are produced. THF may be reused as a material for supplying 5,10-methylene THF. In the embodiment where formaldehyde is used to reproduce 5,10-methylene THF, it is preferable that a slight amount of formaldehyde is sequentially added to the reaction system. Since formaldehyde has a high reactivity, the sequential addition thereof to keep pace with the consumption of 5,10-methylene THF may result in suppression of by-product production.

Moreover, as shown in the example in FIG. 1, the method of the present invention for producing β-hydroxy amino acid is suitable for preferentially producing the L-isomer of the amino acid when using a predetermined enzyme. The phrase "for preferentially producing the L-isomer" means that the ratio of the L-isomer of the resulting β-hydroxy amino acid is higher than that of the D-amino acid. The ratio of L-isomer is preferably 70% or more, further preferably 80% or more, and still further preferably 90% or more. The ratio of the L-isomer in the serine derivative may be calculated by the expression ([L-isomer]/([D-isomer]+[L-isomer]))*100.

The reaction temperature is preferably 10 to 50° C. and more preferably 20 to 40° C. The pH value for the reaction system is preferably 5 to 9 and more preferably 6 to 8.

According to the method of the present invention, 5,10-methylene THF and/or the aldehyde of formula (II) is reacted with D-α-amino acid in the presence of a predetermined enzyme. The enzyme which catalyzes the reaction may be obtained from a microorganism belonging to genera *Paracoccus, Aminobacter*, or *Ensifer*. More specific examples of these microorganisms may include *Paracoccus* sp., *Aminobactor* sp., and *Ensifer* sp. and preferably *Paracoccus* sp. FERM BP-10604, *Aminobactor* sp. FERM BP-10605, and *Ensifer* sp. FERM BP-10606.

The strains having a FERM number assigned are deposited strains as mentioned below and therefore, may be available by referencing to its associated number and the following procedure. These strains were each converted into an International Deposit under the provisions of the Budapest Treaty on May 11, 2006.

(1) Name: *Paracoccus* sp. AJ110402
Deposit number: FERM BP-10604
Depositary authority: International Patent Organism Depositary, National Institute of Advanced Industrial Science and Technology
Address: Chuoh No. 6, Higashi 1-1-1, Tsukuba, Ibaraki, Japan
Deposit date: Mar. 8, 2005

(2) Name: *Aminobactor* sp. AJ110403
Deposit number: FERM BP-10605
Depositary authority: International Patent Organism Depositary, National Institute of Advanced Industrial Science and Technology
Address: Chuoh No. 6, Higashi 1-1-1, Tsukuba, Ibaraki, Japan
Deposit date: Mar. 8, 2005

(3) Name: *Ensifer*. sp. AJ110404
Deposit number: FERM BP-10606
Depositary authority: International Patent Organism Depositary, National Institute of Advanced Industrial Science and Technology
Address: Chuoh No. 6, Higashi 1-1-1, Tsukuba, Ibaraki, Japan
Deposit date: Mar. 8, 2005

More specifically, examples of the enzymes used in the reaction for producing the β-hydroxy amino acid in the present invention may include the following proteins:

(A) a protein having an amino acid sequence of SEQ ID NO: 5;

(B) a variant of the protein having the amino acid sequence of SEQ ID NO: 5, which is able to catalyze the reaction to produce the β-hydroxy amino acid of formula (III);

(C) a protein having an amino acid sequence of SEQ ID NO: 11;

(D) a variant of the protein having the amino acid sequence of SEQ ID NO: 11, which is able to catalyze the reaction to produce the β-hydroxy amino acid of formula (III);

(E) a protein having an amino acid sequence of SEQ ID NO: 16;

(F) a variant of the protein having the amino acid sequence of SEQ ID NO: 16, which is able to catalyze the reaction to produce the β-hydroxy amino acid of formula (III).

The use of any of the aforementioned proteins may achieve efficient production of the β-hydroxy amino acid. According to the method of the present invention, among the β-hydroxy amino acids, the L-amino acid form which has an asymmetric carbon in the α-position may be produced with high selectivity. In particular, in the system where D-α-alanine reacts with 5,10-methylene THF, α-methyl-L-serine only may be substantially produced, which leads to efficient production of the optically-active amino acid.

The protein having the amino acid sequence of SEQ ID NO: 5 may be isolated from the *Paracoccus* sp. FERM BP-10604 strain. The protein having the amino acid sequence of SEQ ID NO: 11 may be isolated from the *Aminobacter* sp. BP-10605 strain. The protein having the amino acid sequence of SEQ ID NO: 16 may be isolated from *Ensifer* sp. FERM BP-10606 strain.

As mentioned above, according to the method of the present invention, proteins which are substantially the same as the proteins (A), (C), and (E), for example, variant proteins, may also be used. For example, protein (B) is a variant of, or substantially the same as, protein (A). A variant protein may have one or more mutations in the amino acid sequence including substitutions, deletions, insertions, additions, and inversions within the sequence. The number of mutations may be one or more, and may vary depending on the position of the amino acid residue to be mutated in the protein structure and type of the amino acid residue, and may be a number which does not substantially affect the protein structure and activity. Specifically, the number of mutations may be 1 to 50, preferably 1 to 30, and more preferably 1 to 10. However, the variant protein (B) may desirably have an activity which is approximately half or more, preferably 80% or more, more preferably 90% or more, and still more preferably 95% or more of the enzyme activity compared with protein (A) under conditions of 30° C., pH6.5 to 8.0.

The mutations in the amino acid sequence of protein variant (B) may be achieved by alternating the nucleotide sequence so that the amino acid at the specific site of the gene encoding the protein is substituted, deleted, inserted, or added using, e.g., the site-specific mutagenic method. Alternatively, the polynucleotide having the nucleotide sequence altered as mentioned above may be obtained through the known conventional mutation process. The mutation process may include an in vitro treatment of the DNA encoding protein (A) with hydroxyamine or the like, and a method in which a microorganism belonging to genus *Escherichia* which carries DNA encoding protein (A) is treated by means of UV irradiation or with a mutagenic agents commonly used for artificial mutation such as N-methyl-N'-nitro-N-nitrosoguanidine (NTG) and nitrous acid.

The aforementioned mutations may also include naturally-occurring mutations, such as differences between species or between strains of a microorganism. By expressing the DNA having the mutation(s) mentioned above in appropriate cells and examining the enzyme activity of the expressed products, the DNA encoding the protein which is a variant of, or substantially the same protein as, protein (A) may be obtained.

Like the relationship between proteins (A) and (B), protein (D) is an example of a protein variant which is substantially the same as protein (C), and protein (F) is an example of protein variant which is substantially the same as protein (E).

Other examples of protein variants which are substantially the same as proteins (A), (B), and (C) may be proteins which have an amino acid sequence resulting in homology of preferably 70% or more, more preferably 80% or more, and still more preferably 90%, and most preferably 95% or more with respect to proteins (A), (B) and (C). In the present specification, the homology of the amino acid sequence may be obtained by calculating a matching count percentage over the full-length of the polypeptide coded into ORF, using GENE-TYX software Ver7.0.9 (Genetics) with Unit Size to Compare=2, or by its equivalent calculation method.

The present invention also provides polynucleotides encoding the aforementioned proteins. Due to codon degeneracy, a certain amino acid sequence may be defined by more than one nucleotide sequence. That is, the polynucleotide of the present invention includes polynucleotides having nucleotide sequences which encode any of the aforementioned proteins (A), (B), (C), (D), (E), and (F).

Specifically, examples of the polynucleotide of the present invention may include the following polynucleotides:

(a) a polynucleotide having a nucleotide sequence of SEQ ID NO: 4;

(c) a polynucleotide having a nucleotide sequence of SEQ ID NO: 10; and (e) a polynucleotide having a nucleotide sequence of SEQ ID NO: 15.

The polynucleotide of (a) encodes the protein (A), and may be isolated from the *Paracoccus* sp. FERM BP-10604 strain. The polynucleotide (c) encodes the protein (C), and may be isolated from the *Aminobacter* sp. FERM BP-10605 strain. The polynucleotide (e) encodes the protein (E), and may be isolated from the *Ensifer* sp. FERM BP-10606 strain.

Taking the polynucleotide (a) as an example, a method for isolating the polynucleotides will be described. The DNA having the nucleotide sequence of SEQ ID NO: 4 may be obtained from a chromosomal DNA of *Paracoccus* sp. or a DNA library by PCR (polymerase chain reaction, see White, T. J. et al; Trends Genet., 5, 185 (1989)) or hybridization. The primer used for PCR may be designed based on, for example, the internal amino acid sequence of a purified protein which is able to catalyze the reaction involved in the method of the present invention. Alternatively, the primer or the probe for hybridization may be designed based on the nucleotide sequence of SEQ ID NO: 4, and the DNA may be isolated using the probe. A combination of a primer having a sequence corresponding to a 5' non-translation domain and another primer having a sequence corresponding to 3' non-translation domain, between which lies a coding domain, may be used for the primer for PCR to amplify the full-length of the protein coding domain.

The primer may be synthesized in the usual manner, for example, by the phosphoramidite method (see Tetrahedron Letters (1981), 22, 1859) using DNA synthesizing equipment Model 380B (Applied Biosystems). The PCR process may be performed using, for example, Gene Amp PCR System 9600 (PERKIN ELMER) and TaKaRa LA PCR in vitro Cloning Kit (TaKaRa Bio) according to the method specified by the manufacturer.

The polynucleotides which are substantially the same as the aforementioned polynucleotides (a), (c), and (e) are also included in the polynucleotide of the present invention. The polynucleotides (b), (d) and (f) described below may be enumerated as examples of the polynucleotide which are substantially the same as the polynucleotides (a), (c) and (e), respectively.

Polynucleotide (b) is able to hybridize with a nucleotide sequence complementary to that of SEQ ID NO: 4 under stringent conditions, and encodes a protein which is able to catalyze the reaction of a D-α-amino acid of formula (I) with 5,10-methylene THF and/or an aldehyde of formula (II) to produce β-hydroxy amino acid of formula (III); Polynucleotide (d) is able to hybridize with a nucleotide sequence complementary to that of SEQ ID NO: 10 under stringent conditions, and encodes a protein which is able to catalyze the reaction of a D-α-amino acid of formula (I) with 5,10-methylene THF and/or an aldehyde of formula (II) to produce β-hydroxy amino acid of formula (III); Polynucleotide (f) is able to hybridize with a nucleotide sequence complementary to that of SEQ ID NO: 15 under stringent conditions, and encodes a protein which is able to catalyze the reaction of a D-α-amino acid of formula (I) with 5,10-methylene THF and/or an aldehyde of formula (II) to produce β-hydroxy amino acid of formula (III).

For the polynucleotide to be hybridized, a probe, for example, may be used. In each case, the probe may be prepared in the usual manner based on the nucleotide sequences of SEQ ID Nos. 4, 10, and 15. The objective polynucleotide may be isolated by picking out the nucleotide to be hybridized using the probe in the usual manner. The DNA probe, for example, may be prepared by amplifying the nucleotide sequences cloned into plasmid or a phage vector, cutting out the desired nucleotide sequence for the probe by a restriction enzyme, and then extracting the sequence. The portion to be cut out may be adjusted according to the objective DNA. Once the polynucleotide which is substantially the same has been detected, the polynucleotide may be amplified in the usual manner such as PCR.

The "stringent conditions" mean conditions under which a so-called specific hybrid is formed but a nonspecific hybrid is not formed. Although it is difficult to clearly define the condition in terms of numerical values, an example of such conditions may be those under which the DNAs having high homology, for example, 50% or more, preferably 70% or more, more preferably 80% or more, further preferably 90% or more, and still further preferably 95% or more, are hybridized while the DNAs having lower homology are not hybridized. The homology (%) of the nucleotide sequences is represented by numeric values obtained by percentage calculation over the full-length of ORF of each gene (including a stop codon) using GENETYX software Ver7.0.9 (Genetics) with Unit Size to Compare=6, pick up location=1. As another example, stringent conditions may be those of ordinary washing conditions in Southern hybridization, under which the DNAs are hybridized at 60° C. and salt concentration of 1×SSC, 0.1% SDS, and preferably 0.1×SSC, 0.1% SDS. The genes hybridized under such conditions may include a gene containing a stop codon or a gene without activity due to a mutation in the activity center region. However, these may be easily screened off by inserting the obtained genes in a commercially-available expression vector, expressing the genes in an appropriate host, and determining the enzyme activity of the expressed product by a method described later.

As mentioned above, in the case of the aforementioned polynucleotide (b), the protein encoded thereby may desirably have an activity of approximately half or more, preferably 80% or more, and more preferably 90% or more of the activity of protein (A), which is encoded by the nucleotide sequence of SEQ ID NO: 4 under conditions of 30° C., pH8.0. Similarly, in the case of the aforementioned polynucleotide (d), the protein encoded thereby may desirably have the activity to the same extent as the above with respect to the protein (C). In the case of the aforementioned polynucleotide (f), the protein encoded thereby may desirably have the activity to the same extent as the above with respect to the protein (E).

According to the method of the present invention, the enzyme may be used in any form as long as it is capable of catalyzing the aforementioned reaction in the reaction system. Examples of the specific forms thereof may include a cultured product of enzyme-producing microorganism, cells of the microorganism separated from the cultured product, and a processed cell product. The cultured product of the microorganism is a product obtained by culturing the microorganism. More specifically, the cultured product is a mixture containing the cells of the microorganisms, the cultivation medium used for culturing the microorganism, and the substances produced by the cultured microorganism. The cells of the microorganisms may be washed before using as the washed cells. The processed cell product may be disrupted, lysed, and/or freeze-dried cells, as well as a crude-purified protein that is collected from the processed cells, and a purified protein that is further purified. As for the purified proteins, a partially-purified protein which is obtained by a variety of types of purification methods may be used. Alternatively, a fixed protein which is fixed by a covalent bond method, an adsorption method, or an entrapment method may be used. Depending on the employed microorganism, a part of the cells may be lysed during cultivation. In this case, the supernatant of the cultivation medium may also be used as an enzyme-containing substance.

Now, the method for producing the proteins of the present invention and the method for preparing the recombinants and transformants used in producing the proteins will be described hereinbelow using the aforementioned protein (A) as an example. The methods which will be described below are also applicable to other proteins.

The transformant which expresses the aforementioned protein (A) may be prepared using a recombinant polynucleotide which contains the polynucleotide having the aforementioned nucleotide sequence (a) incorporated therein. For example, the transformant may be obtained by preparing a recombinant DNA containing the DNA having the nucleotide sequence of SEQ ID NO: 4, and then introducing the resulting recombinant DNA into an appropriate host. Examples of the host for expressing the protein identified by the DNA having the nucleotide sequence of SEQ ID NO: 4 may include a variety of prokaryotic cells, including microorganisms belonging to genus *Escherichia* such as *Escherichia coli*, microorganisms belonging to genus *Corynebacterium, Bacillus subtilis*, and a variety of eukaryotic cells including *Saccharomyces cerevisiae, Pichia stipitis*, and *Aspergillus oryzae*. Using the host which may be easily handled without any expensive components upon cultivation, β-hydroxy amino acid may be easily produced on a large scale.

The recombinant DNA for introducing the DNA having the nucleotide sequence of SEQ ID NO: 4 into a host may be prepared by inserting the DNA into a vector suitable for the type of the host so that the inserted DNA can express the protein encoded thereby. If the promoter inherently exists with the gene encoding the aforementioned enzyme derived or isolated from, e.g., *Paracoccus* sp., *Aminobacter* sp., and *Ensifer* sp. are capable of functioning in the host cells, such a promoter may be used as the promoter for facilitating the expression of the proteins. Alternatively, if necessary, any other promoter which can function in the host may be coupled to the DNA of SEQ ID NO: 4 or the like so that the proteins are expressed under the control of the promoter.

Examples of methods for transforming the recombinant DNA to introduce the recombinant DNA into the host cell may include the D. M. Morrison's method (Methods in Enzymology 68, 326 (1979)) and a method for improving the permeability of the DNA by treating a recipient cell with calcium chloride (Mandel, M. and Higa, A., J. Mol. Biol., 53, 159 (1970)).

In the case of producing an objective protein on a large scale using the recombinant DNA technology, one of the preferable embodiments may be the formation of an inclusion body of the protein. The inclusion body is configured by aggregation of the protein in the protein-producing transformant. The advantages of this expression production method may be protection of the objective protein from digestion due to protease in the microbial cells, and ready purification of the objective protein that may be performed by disruption of the microbial cells and following centrifugation. To obtain the active protein from the protein inclusion body, a series of manipulations such as solubilization and activity regeneration is required, and thus, the manipulations are more complicated than those used when directly producing the active protein. However, when a protein which affects microbial cell growth is produced on a large scale in the microbial cells, effects thereof may be avoided by accumulating the protein as an inactive inclusion body in the microbial cells.

Examples of the methods for producing the objective protein on a large scale as an inclusion body may include methods of expressing the protein alone under the control of a strong promoter, as well as methods of expressing the objective protein as a fusion protein with a protein known to be expressed in a large amount.

As the host to be transformed, any strain commonly used in expressing heterogenes may be used. Suitable examples thereof may include the *Escherichia coli* JM109, DH5α, HB101, and BL21 strains, which are subspecies of the *Escherichia coli* K12 strain. The method for transforming the host and the method for selecting out the transformants are described in Molecular Cloning: A Laboratory Manual, 3rd edition, Cold Spring Harbor press (Jan. 15, 2001). An example of the method for preparing the transformed *Escherichia coli* strain and producing a predetermined enzyme using the transformed strain will be specifically described hereinbelow.

As the promoter for expressing the DNA encoding the mutant protein, the promoters typically used for producing xenogenic proteins in *E. coli* may be used, and examples thereof may include strong promoters such as T7 promoter, lac promoter, trp promoter, trc promoter, tac promoter, and PR promoter and PL promoter of lambda phage. As the vector, pUC19, pUC18, pBR322, pHSG299, pHSG298, pHSG399, pHSG398, RSF1010, pMW119, pMW118, pMW219, pMW218, pACYC177, pACYC184, and derivatives thereof may be used. Other vectors of phage DNA may also be used. In addition, expression vectors which contain a promoter and can express the inserted DNA sequence may also be used.

In order to produce the mutant protein as a fusion protein inclusion body, a fusion protein gene is produced by linking a gene encoding another protein, preferably a hydrophilic peptide, upstream or downstream of the mutant protein gene. Such a gene encoding another protein may be those which increase the amount of the accumulated fusion protein and enhance solubility of the fusion protein after denaturation and regeneration steps. Examples of candidates thereof may include T7 gene 10, β-galactosidase gene, dehydrofolic acid reductase gene, interferon γ gene, interleukin-2 gene and prochymosin gene.

Such a gene may be ligated to the gene encoding the mutant protein so that reading frames of codons are matched. This may be effected by ligating at an appropriate restriction enzyme site or using a synthetic DNA having an appropriate sequence.

In some cases, it is preferable to ligate a terminator, i.e. the transcription termination sequence, downstream of the fusion protein in order to increase the production amount. Examples of this terminator may include T7 terminator, fd phage terminator, T4 terminator, tetracycline resistant gene terminator, and *E. coli* trpA gene terminator.

The vector for introducing the gene encoding the mutant protein or the fusion protein of the mutant protein with the other protein into *E. coli* may preferably be of a so-called multicopy type. Examples thereof may include plasmids having a replication origin derived from ColE1, such as pUC based plasmids, pBR322 based plasmids or derivatives thereof. As used herein, the "derivative" means the plasmid modified by the substitution, deletion, insertion, addition and/or inversion of the nucleotides. "Modified" referred to herein includes the modification by mutagenesis with the mutagen or UV irradiation and natural mutation.

In order to select the transformants, it is preferable to employ a vector having a marker such as an ampicillin resistant gene. As such a plasmid, expression vectors having the strong promoter are commercially available (pUC series: Takara Shuzo Co., Ltd., pPROK series and pKK233-2: Clontech, etc.).

A DNA fragment where the promoter, the gene encoding the protein having the objective activity or the fusion protein of the objective protein with the other protein, and in some cases the terminator are ligated sequentially, is then ligated to the vector DNA to obtain a recombinant DNA.

The resulting recombinant DNA is used to transform *Escherichia coli* and then the transformed *Escherichia coli* is cultured, to express and produce the predetermined protein or its fused protein.

In the case of expressing the fusion protein, the fusion protein may be composed so as to be able to cleave out the objective enzyme therefrom using a restriction protease which recognizes a sequence of blood coagulation factor Xa, kallikrein or the like which is not present in the objective enzyme.

As production media, media such as M9-casamino acid medium and LB medium which are typically used for cultivation of *E. coli* may be used. The conditions for cultivation and a production induction may be appropriately selected depending on types of the marker and the promoter of the vector and the host used.

The following methods are available for recovering the objective protein or the fusion protein containing the objective protein with the other protein. If the objective protein or the fusion protein thereof is solubilized in the microbial cells, the cells may be collected and then disrupted or lysed to thereby obtain a crude enzyme solution for use. If necessary, the crude solution may be purified using techniques such as ordinary precipitation, filtration and column chromatography, to obtain the purified objective protein or the fusion protein. In this case, the purification may be performed using an antibody against the mutant protein or the fusion protein. In the case where the protein inclusion body is formed, it may be solubilized with a denaturant, and then the denaturant may be removed by means of dialysis or the like to obtain the objective protein.

EXAMPLES

The present invention will be described in more detail with reference to the following non-limiting examples.

Example 1

Detection of 2-methylserine Hydroxylmethyl Transferase Activity

In a nutrient broth agar medium (Difco), microorganisms listed in Table 1 were cultured at 30° C. for 24 hours. A platinum loopful of the resulting cells were inoculated into 3 ml of nutrient broth liquid medium and then cultured at 30° C. for 24 hours, with 120 reciprocations/minute. 0.15 ml of the resulting cultured solution was inoculated into 3 ml of nutrient broth liquid medium containing 0.2% α-methyl-DL-serine and cultured at 30° C. for 24 hours with 120 reciprocations/minute.

After cultivation, the cells were centrifuged and then washed twice with an equal volume of 50 mM potassium phosphate buffer (pH7.4) containing 0.1 mM pyridoxal phosphoric acid. 50 mM potassium phosphate buffer (pH7.4) containing 0.1 mM pyridoxal phosphoric acid was used to prepare a total amount (0.3 ml) of cell suspension and then the suspension was ultrasonically disrupted at 4° C. The supernatant obtained by centrifugation (16,000 g, 10 min.) was dialyzed with 50 mM potassium phosphate buffer (pH7.4) containing 0.1 mM pyridoxal phosphoric acid to obtain a cell-free extracted solution.

0.05 ml of cell-free extracted solution was added to a reaction solution (1), which has a composition of 50 mM potassium phosphate buffer (pH7.4), 10 mM α-methyl-DL-serine, 0.5 mM tetrahydrofolic acid, 10 mM 2-mercaptoethanol, 0.01 mM pyridoxal phosphoric acid, 10 mM sodium ascorbate, 0.4 mM NADP, and 1 U/ml 5,10-methylene tetrahydrofolic acid dehydrogenase. The total amount (0.1 ml) of solution was reacted at 30° C. for 10 minutes. The reaction was stopped with 0.15 ml of 0.6 N hydrochloric acid. The supernatant obtained by centrifugation (16,000 g, 10 minutes) was left to stand at room temperature for 10 minutes. Absorbance (E11) of the supernatant caused by 5,10-methenyl-5,6,7,8-tetrahydrofolic acid was measured at 350 nm. As a control, another reaction was performed in the same way as the above, except that α-methyl-DL-serine was replaced with water in the aforementioned solution (1), and the absorbance (E10) caused by 5,10-methenyl-5,6,7,8-tetrahydrofolic acid in the resulting liquid was measured. Based on the measured absorbance, the alteration in the absorbance specific to α-methyl-DL-serine (EΔ1=E11−E10) was calculated. The results are shown in Table 1.

TABLE 1

| Strain | EΔ1 |
|---|---|
| *Paracoccus* sp. A13 | 1.35 |

TABLE 1-continued

| Strain | EΔ1 |
|---|---|
| *Aminobacter* sp. A10 | 2.07 |
| *Ensifer* sp. B30 | 1.25 |

Example 2

Purification of 2-methyl Serine Hydroxylmethyl Transferase Derived from the *Paracoccus* sp. AJ110402 Strain (1) Preparation of Cell-free Extracted Solution Cells of *Paracoccus* species were cultured in the nutrient broth agar medium (Difco) at 30° C. for 24 hours. The cultured cells were inoculated into 50 ml of nutrient broth liquid medium in a 500 ml Sakaguchi flask and cultured at 30° C. for 24 hours with 120 reciprocations/minute. The resulting cultured solution was inoculated into 2 L of liquid medium containing 0.2% α-methyl-DL-serine, and 0.17% yeast nitrogen base w/o amino acid and ammonium sulfate (pH7.0). 50 ml each of the mixture was dispensed into each of the 500 ml Sakaguchi flasks, and then cultured at 30° C. for 22 hours with 120 reciprocations/minute. The resulting cells were collected by centrifugation (8,000 g, 10 minutes) and washed twice with 25 mM potassium phosphate buffer containing 0.02 mM pyridoxal phosphoric acid (referred to hereinafter as the buffer (I)). Then, 100 ml of cell suspension was prepared using the buffer (I). The cells were ultrasonically disrupted and centrifuged (18,000 g, 10 minutes), and the resulting supernatant was ultra-centrifuged (200,000 g, 30 minutes). The resulting supernatant was used as the cell-free extracted solution.

(2) Anion-exchange Chromatography

The cell-free extracted solution was applied to a ResourceQ column (Amersham Biosciences) which had been previously equilibrated with the buffer (I), and the enzyme was eluted by a linear concentration gradient of 0-1M sodium chloride. This process was conducted twice by dividing the cell-free extracted solution into two aliquots.

(3) Hydrophobic Interaction Chromatography

Active fractions of the enzyme obtained in the aforementioned (2) were mixed with the buffer (I) containing an equivalent amount of 2M ammonium sulfate and then applied to the Phenyl-Sepharose column (Amasham Biosciences) which had been previously equilibrated with the buffer (I) containing 1M ammonium sulfate. Then, the enzyme was eluted by the linear concentration gradient of 1-0M ammonium sulfate.

(4) Hydroxyapatite Column Chromatography

The active fractions obtained in the aforementioned (3) were dialyzed with the 2.5 mM potassium phosphate buffer (pH6.8) containing 0.02 mM pyridoxal phosphoric acid and then applied to the CellulofineHAp columns (SEIKAGAKU Corp.) which had been previously equilibrated with the same buffer. The enzyme was eluted with the 2.5-250 mM potassium phosphate buffer (pH6.8). The active fractions of the enzyme were used as the purified enzyme in the following experiments.

The enzyme thus obtained in this way had specific activity of 3.51 U/mg. The enzyme was electrophoresed in SDS-polyacrylamide and the gel was stained with a Coomassie brilliant blue staining fluid. A homogeneous band appeared at a position of the molecular weight of approximately 47,000.

Example 3

Determination of the Amino Acid Sequence of 2-methyl Serine Hydroxylmethyl Transferase Derived from the *Paracoccus* sp. AJ110402 Strain and the Nucleotide Sequence Encoding the Same 50 pmol of the purified enzyme which had been prepared in Example 2 was electrophoresed in SDS-polyacrylamide, and transferred on a PVDF membrane. The relevant part was put in a protein sequencer to determine 30 amino acids (SEQ ID NO: 1).

Subsequently, 5 μg of genome DNA derived from the *Paracoccus* sp. AJ110402 strain was cleaved with PstI (50 U) and then ligated to the PstI cassette of TaKaRa LA PCR in vitro Cloning Kit in accordance with the kit directions. Using the ligated mixture as a template, PCR (94° C.: 30 sec., 47° C.: 2 min., 72° C.: 1 min., 30 cycles) was performed with a cassette primer C1 and a primer HMT_FW1 (SEQ ID NO: 2). Using the PCR reaction solution as a template, the second PCR (94° C.: 30 sec., 55° C.: 2 min., 72° C.: 1 min., 30 cycles) was performed with a cassette primer C2 and a primer HMT_FW2 (SEQ ID NO: 3). Approximately 0.7 kb-length fragments, of which amplification had been confirmed, were ligated to pGEM-Teasy (Promega), with which *Escherichia coli* JM109 strain was then transformed. The nucleotide sequence of the plasmid having the objective fragment was confirmed with a DNA sequencer (ABI3100). Approximately 1.1 kb-length gene fragment was obtained by treating the plasmid with EcoRI/PstI. Using the fragment as a probe, chromosomal DNAs were subjected to Southern analysis after treatment with various types of restriction enzymes. When the treatment was performed with BglII/NruI, a positive signal was confirmed in an approximately 3.5 kb region.

Subsequently, the chromosomal DNAs were treated with BglII/NruI and then electrophoresed in an agarose gel, to purify the approximately 3.5 kb fragment. The fragment was then ligated to the pUC19 BamHI/SmaI site. Using this reaction solution, *Escherichia coli* JM109 was transformed to create a library. The aforementioned probe was used to perform colony hybridization for obtaining positive colonies. A plasmid was extracted from the positive colonies. The plasmid was designated pHMT01. As to the inserted 3475 bp part, the nucleotide sequence thereof was determined. As a result, an ORF (SEQ ID NO: 4) composed of 425 amino acids was found. The ORF had the same sequence as the amino acid sequence obtained from N-terminal analysis, which confirms that the objective gene was obtained. As for the ORF of the gene sequence, a homology search was conducted. As a result, 55% homology was confirmed between serine hydroxylmethyl transferase derived from *Methylobacterium extorquens* and the ORF amino acid sequence.

Example 4

Expression of 2-methylserine Hydroxylmethyl Transferase Gene Derived from the *Paracoccus* sp. AJ110402 Strain in *Escherichia coli*

Using pHMT01 as a template, PCR was performed with a primer PHMT_SD_Eco (SEQ ID NO: 6) and a primer PHMT_ter2_Hind (SEQ ID NO: 7) to amplify a 1.2 kb region of 2-methylserine hydroxylmethyl transferase. The amplified sequence was treated with EcoRI/HindIII, and then ligated to pUC18 which had been previously treated with EcoRI/HindIII. With the ligated product, *Escherichia coli* JM109 strain was transformed. A transformant having plasmid (pUCPHMT01) containing the objective gene fragment was thus obtained. The transformant was designated JM109/pUCPHMT01.

JM109/pUCPHMT01 was pre-cultured in the LB medium containing 100 mg/L ampicillin at 37° C. for 16 hours. 2.5 ml of the pre-cultured solution was inoculated into 50 ml of the LB medium containing 100 mg/L ampicillin and cultured at 37° C. One hour after the onset of the cultivation, IPTG was added so that the final concentration thereof reached 1 mM. The mixture was further cultured for four hours. The resulting cells were collected by centrifugation and washed with the 50 mM phosphoric acid buffer (pH7.4) containing 0.1 mM pyridoxal phosphoric acid. A cell suspension was then prepared using the same buffer. The cells were ultrasonically disrupted and centrifuged (18,000 g, 10 min., 4° C.) to obtain a supernatant. 2-methylserine hydroxylmethyl transferase activity was measured as to the supernatant as the cell-free extracted solution. The measured value was 3.02 U/mg. Apart from the above, pUC18 was introduced into JM109 strain to obtain a transformant JM109/pUC18, and a cell-free extracted solution was prepared therefrom and the activity was measured in the same manner as described above. The measured activity was less than the detection limit.

Example 5

Isolating the 2-methylserine Hydroxylmethyl Transferase Gene from the *Aminobactor* sp. AJ110403 Strain Using the genomic DNA prepared from the *Aminobactor* sp. AJ110403 strain as a template, PCR was performed with mixed primers HMT_MIX_FW1 (SEQ ID NO: 8) and HMT_MIX_RV2 (SEQ ID NO: 9). An amplified fragment of 0.6 kb was confirmed. Using this PCR product as a probe, the genome DNA of the *Aminobactor* sp. AJ110403 strain was subjected to BamHI treatment and Southern analysis. As a result, a positive signal appeared in a 3.5 kb-length region.

Subsequently, the genomic DNA of the *Aminobactor* sp. AJ110403 strain was treated with BamHI and electrophoresed in the agarose gel. A fragment of approximately 3.5 kb was purified. The fragment was ligated to the pUC118 BamHI site. Using this reaction solution, *Escherichia coli* JM109 was transformed to create a library. The aforementioned probe was used to perform colony hybridization for obtaining positive colonies, and a plasmid was extracted from the positive colonies. The plasmid was designated pAHMT01. As for the inserted part in the plasmid, the nucleotide sequence thereof was determined. As a result, existence of an ORF composed of 425 amino acids was confirmed (SEQ ID NO: 10).

Using pAHMT01 as a template, PCR was performed with primers A2_Bam (SEQ ID NO: 12) and A2_ter_Pst (SEQ ID NO: 13). The amplified fragment of 1.2 kb obtained by PCR was treated with BamHI/PstI, and then inserted into pUC18 BamHI/PstI site, to obtain pUCAHMT01. Using this plasmid, *Escherichia coli* JM109 was transformed. The transformant was designated JM109/pUCAHMT01.

JM109/pUCAHMT01 was pre-cultured in the LB medium containing 100 mg/L ampicillin at 37° C. for 16 hours. 2.5 ml of pre-cultured solution was inoculated into 50 ml of the LB medium containing 100 mg/L ampicillin and cultured at 37° C. One hour after the onset of the cultivation, IPTG was added so that the final concentration thereof reached 1 mM. The mixture was further cultured for four hours. The resulting cells were collected by centrifugation and washed with the 50 mM phosphoric acid buffer (pH7.4) containing 0.1 mM pyridoxal phosphoric acid. A cell suspension was then prepared using the same buffer. The cells were ultrasonically disrupted and centrifuged (18,000 g, 10 min., 4° C.) to obtain a supernatant. 2-methylserine hydroxylmethyl transferase activity was measured as to the supernatant as the cell-free extracted solution. The measured value was 0.27 U/mg. The activity as to the cell-free extracted solution prepared from JM109/pUC18 in the same manner as described above was less than the detection limit.

Example 6

Isolating 2-methylserine Hydroxylmethyl Transferase Gene from the *Ensifer* sp. AJ110404 Strain Using genomic DNA prepared from the *Ensifer* sp. AJ110404 strain as a template, PCR was performed with mix primers HMT_MIX_FW2 (SEQ ID NO: 14) and HMT_MIX_RV2 (SEQ ID NO: 9). An amplified fragment of 0.6 kb was confirmed. Using this PCR product as a probe, the genomic DNA from the *Ensifer* sp. AJ strain was subjected to EcoRI treatment and Southern analysis. As a result, a positive signal appeared in a 5 kb-length region.

Subsequently, genomic DNA from the *Ensifer* sp. AJ 110404 strain was treated with EcoRI and electrophoresed in the agarose gel. A fragment of approximately 5 kb was purified. The fragment was ligated to the pUC118 EcoRI site. Using this reaction solution, *Escherichia coli* JM109 was transformed to create a library. The aforementioned probe was used to perform colony hybridization for obtaining positive colonies, and a plasmid was extracted from the positive colonies. The plasmid was designated pEHMT01. As to the inserted part in the plasmid, the nucleotide sequence thereof was determined. As a result, existence of an ORF composed of 425 amino acids was confirmed (SEQ ID NO: 15).

Using pEHMT01 as a template, PCR was performed with primers B_Eco (SEQ ID NO: 17) and B_ter_Bam (SEQ ID NO: 18). The amplified fragment of 1.2 kb obtained by PCR was treated with BamHI/EcoRI, and then inserted into pUC18 BamHI/EcoRI site, to obtain pUCEHMT01. Using this plasmid, *Escherichia coli* JM109 was transformed. The transformant was designated JM109/pUCEHMT01.

JM109/pUCEHMT01 was pre-cultured in the LB medium containing 100 mg/L ampicillin at 37° C. for 16 hours. 2.5 ml of pre-cultured solution was inoculated into 50 ml of the LB medium containing 100 mg/L ampicillin and cultured at 37° C. One hour after the onset of the cultivation, IPTG was added so that the final concentration thereof reached 1 mM. The mixture was further cultured for four hours. The resulting cells were collected by centrifugation and washed with the 50 mM phosphoric acid buffer (pH7.4) containing 0.1 mM pyridoxal phosphoric acid. A cell suspension was then prepared using the same buffer. The cells were ultrasonically disrupted and centrifuged (18,000 g, 10 min., 4° C.) to obtain a supernatant. 2-methylserine hydroxylmethyl transferase activity was measured as to the supernatant as the cell-free extracted solution. The measured value was 0.10 U/mg. The activity as to the cell-free extracted solution prepared from JM109/pUC18 in the same manner as described above was less than the detection limit.

Example 7

Production of α-methyl-L-serine with 2-methylserine Hydroxylmethyl Transferase Isolated from *Paracoccus* sp. AJ110402

The purified enzyme solution which was prepared in Example 2 was added to a composition composed of 100 mM D-alanine, 20 mM formaldehyde, 0.5 mM tetrahydrofolic acid, 10 mM sodium ascorbate, 10 mM 2-mercaptoethanol, 0.1 mM pyridoxal phosphoric acid, and 50 mM phosphoric acid buffer (pH7.4), so that the final concentration of the enzyme reached 47 μg/ml. The reaction was performed at 30° C. for 16 hours. As formaldehyde, the highest quality formaldehyde liquid [code No.: 16223-55] from Nakarai Tesque was used.

After the reaction, an equivalent amount of 2 mM aqueous copper sulfate was added thereto and HPLC was performed using Sumichiral OA-6100 (Sumika Chemical Analysis Service, Ltd.) (mobile phase: 1 mM aqueous copper sulfate, column temperature: 40° C., flow rate: 1 min., detection: UV215 nm). As a result, 19 mM of α-methyl-L-serine was detected but no peak attributed to α-methyl-D-serine was detected.

Example 8

Production of α-methyl-L-serine with *Escherichia coli* Expressing the 2-methylserine Hydroxylmethyl Transferase Gene Isolated from *Paracoccus* sp. AJ110402

Using the method described in Example 4, 400 ml of the cultured liquid of JM109/pUCPHMT01 was prepared. After centrifugation, the cells were washed with 50 mM phosphoric acid buffer (pH8.0) containing 0.1 mM pyridoxal phosphoric acid. The cells were added to the 100 ml of reaction solution (150 mM (15 mmol) D-alanine, 0.1 mM pyridoxal phosphoric acid, 0.3 mM tetrahydrofolic acid, 10 mM 2-mercaptoethanol, 20 mM phosphoric acid buffer (pH8.0)) and then 50.5 ml of 600 mM aqueous formaldehyde was added thereto over 24 hours at 30° C. while stirring. As formaldehyde, the highest quality formaldehyde liquid from Nakarai Tesque [code number: 16223-55] was used.

Under the same conditions as those in Example 7, HPLC analysis was performed. As a result, 66.4 mM (9.5 mmol) of α-methyl-L-serine was detected in the reaction solution but the amount of α-methyl-D-serine production was less than the detection limit.

Example 9

Homology of Proteins

Homology was examined for the amino acid sequences of the enzymes obtained in the aforementioned examples. In calculating the homology of the amino acid sequences, Marching count percentage was calculated over the full-length of the polypeptide chain encoded in ORF using GENETYX software Ver7.0.9 (Genetics) with Unit Size to Compare=2.

Amino acid sequences of the following enzymes derived from *Methylobacterium Extorquens* have been deposited as accession No. AAA64456 in GenBank (National Center for Biotechnology Information). Amino acid sequences of the following enzymes derived from *Escherichia coli* have been deposited as accession No. AAA23912 in GenBank.

TABLE 2

|  | Paracoccus sp. SEQ ID NO: 5 | Aminobacter sp. SEQ ID NO: 11 | Ensifer sp. SEQ ID NO: 16 | Methylobacterium Extorquens | E. coli |
|---|---|---|---|---|---|
| Paracoccus sp. SEQ ID NO: 5 Example EC 2.1.2.7 | 100 | 84.7 | 80.0 | 55.5 | 50.4 |
| Aminobacter sp. SEQ ID NO: 11 Example EC 2.1.2.7 |  | 100 | 82.8 | 56.1 | 51.9 |
| Ensifer sp. SEQ ID NO: 16 Example EC 2.1.2.7 |  |  | 100 | 55.8 | 49.3 |
| Methylobacterium Extorquens Comparative example EC 2.1.2.1 |  |  |  | 100 | 59.8 |
| E. coli Comparative example EC 2.1.2.1 |  |  |  |  | 100 |

INDUSTRIAL APPLICABILITY

The method of the present invention is useful in the industries involving in amino acid production. It is expected that the present invention will contribute to the production of various types of β-hydroxy amino acid and optically-active amino acid, and specifically, the method may be used in producing, for example, intermediates for pharmaceuticals.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims along with their full scope of equivalents. Each of the aforementioned documents, including the foreign priority document, is incorporated by reference herein in its entirety.

We claim:

1. A method for producing β-hydroxy amino acid of formula (III):

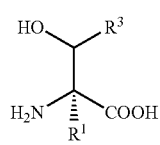

comprising reacting a D-α-amino acid of formula (I):

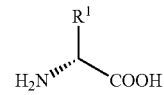

with 5,10-methylenetetrahydrofolic acid,
in the presence of formaldehyde and a protein selected from the group consisting of:
(A) a protein comprising the amino acid sequence of SEQ ID NO: 16;
(B) a variant protein of the amino acid sequence of SEQ ID NO: 16 which is at least 95% homologous to the amino acid sequence of SEQ ID NO: 16, and which is able to catalyze the reaction to produce the β-hydroxy amino acid of formula (III); and wherein $R^1$ is selected from the group consisting of an alkyl group with 1 to 6 carbon atoms, and wherein $R^3$ is hydrogen, and wherein $R^1$ may be either linear or branched, and may have one or more substituents selected from the group consisting of a halogen atom, an alkyl group with up to 3 carbon atoms, an alkoxyl group with up to 3 carbon atoms, a keto group, a hydroxyl group, a thiol group, an amino group, an amido group, an imino group, and a hydrazine group.

2. The method for producing the β-hydroxy amino acid according to claim 1, wherein said D-α-amino acid is D-α-alanine and said β-hydroxy amino acid is α-methyl-L-serine.

3. The method of claim 1, wherein said protein comprising the amino acid sequence of SEQ ID NO. 16, or said variant protein thereof, is a product of a transformant containing a recombinant polynucleotide comprising a polynucleotide encoding said protein.

4. The method of claim 3, wherein said polynucleotide is selected from the group consisting of:
(a) the polynucleotide comprising the nucleotide sequence of SEQ ID NO.: 15;
(b) a polynucleotide which hybridizes with the nucleotide sequence complementary to that of SEQ ID NO: 15 under stringent conditions wherein the stringent conditions are 60° C., 1×SSC and 0.1% SDS.

5. The method for producing the β-hydroxy amino acid according to claim 1, wherein said protein is a protein comprising the amino acid sequence of SEQ ID NO: 16.

6. The method for producing the β-hydroxy amino acid according to claim 2, wherein said protein is a protein comprising the amino acid sequence of SEQ ID NO: 16.

7. The method for producing the β-hydroxy amino acid according to claim 3, wherein said D-α-amino acid is D-α-alanine and said β-hydroxy amino acid is α-methyl-L-serine.

8. The method for producing the β-hydroxy amino acid according to claim 3, wherein said protein is a protein comprising the amino acid sequence of SEQ ID NO: 16.

9. The method for producing the β-hydroxy amino acid according to claim 7, wherein said protein is a protein comprising the amino acid sequence of SEQ ID NO: 16.

10. The method for producing the β-hydroxy amino acid according to claim 4, wherein said D-α-amino acid is D-α-alanine and said β-hydroxy amino acid is α-methyl-L-serine.

11. The method for producing the β-hydroxy amino acid according to claim 4, wherein said protein is a protein comprising the amino acid sequence of SEQ ID NO: 16.

12. The method for producing the β-hydroxy amino acid according to claim 10, wherein said protein is a protein comprising the amino acid sequence of SEQ ID NO: 16.

13. The method for producing β-hydroxy amino acid according to claim 1, wherein $R^1$ is methyl or ethyl.

14. The method for producing β-hydroxy amino acid according to claim 13, wherein said protein comprises the amino acid sequence of SEQ ID NO: 16.

* * * * *